United States Patent [19]

Platé et al.

[11] Patent Number: 6,004,583
[45] Date of Patent: *Dec. 21, 1999

[54] PROTEIN-CONTAINING POLYMER COMPOSITION FOR ORAL ADMINISTRATION

[75] Inventors: Nikolai A. Platé ; Lev I. Valuev; Tatyana A. Valueva; Ludmila K. Staroseltseva; Alexander S. Ametov; Vladimir A. Knyazhev, all of Moscow, Russian Federation; Jay M.S. Henis, St. Louis, Mo.

[73] Assignee: Orex Pharmaceutical Development Corp., St. Louis, Mo.

[*] Notice: This patent is subject to a terminal disclaimer.

[21] Appl. No.: 08/691,617

[22] Filed: Aug. 2, 1996

Related U.S. Application Data

[63] Continuation-in-part of application No. 08/408,076, Mar. 22, 1995.

[51] Int. Cl.$^6$ .............................. A61K 9/10; A61K 31/74; A61K 31/78; A61K 31/79
[52] U.S. Cl. ...................... 424/486; 424/487; 424/78.17; 424/78.18; 424/78.24
[58] Field of Search ..................................... 424/487, 486, 424/78.17, 78.18, 78.24; 525/54.1, 54.2; 530/815, 816

[56] References Cited

U.S. PATENT DOCUMENTS

| | | |
|---|---|---|
| 3,959,080 | 5/1976 | Orth et al. . |
| 4,178,361 | 12/1979 | Cohen et al. . |
| 4,714,768 | 12/1987 | Hewklen et al. . |
| 4,795,436 | 1/1989 | Robinson . |
| 4,849,227 | 7/1989 | Cho . |
| 5,049,545 | 9/1991 | Löbermann et al. . |
| 5,359,030 | 10/1994 | Ekwuribe . |
| 5,438,040 | 8/1995 | Ekwuribe . |
| 5,563,056 | 10/1996 | Swan et al. . |

FOREIGN PATENT DOCUMENTS

| | | |
|---|---|---|
| 0098110 | 1/1984 | European Pat. Off. . |
| 2076733 | 3/1994 | Russian Federation . |
| 1404513 | 2/1988 | U.S.S.R. . |
| 9515352 | 6/1985 | WIPO . |

OTHER PUBLICATIONS

"Polymers for Colon–Specific Drug Delivery", Kopeček et al., Journal of Controlled Release Mar. 19, 1992, Nos. 1/3, Amsterdam, NL, p. 121–130.
"Immobilization of Ovomucoid on Dextrans", Valuev et al., Polymer Science vol. 34 (1992) No. 11, Birmingham, AL.
"Interaction of Polymeric Derivarives of Trypsin with its Portein Inhibitor", Valuev et al., Polymer Science vol. 37 (Sep.1995) , No. 9, Birmingham, AL.
"Hypoglycemic Effect of Novel Oral Microspheres of Insulin with Protease Inhibitor in Normal and Diabetic Rats", Morishita et al, International Journal of Pharmaceutics, 78(1992)9–16.
"Monosubstituted 2,2–Dimethyl–3–Formyl–L–Thiazolidine–4–Carbonyl Insulins", Lindsay et al, Eur. J. Biobhem. 15 (1970) p. 547.
"Evidence that Insulin Activates an Instrinic Plasma Membrane Protease in Generating a Secondary Chemical Mediator", Seales et al, The Journal of Biological Chemistry, vol. 255, No. 14, Issue of Jul. 25, pp. 6529–6531, 1980.
"Polymer Matrices for Oral Delivery", Greenley et al, Polymer Preprints, 1990, v. 31, N2, pp. 182–183.
"Biodegradable Azopolymer Coating for Oral Delivery of Peptide Drugs", Saffran et al, Biochemical Society Transactions 18(5) 752–4 (1990), pp. 752–754.
Thermally Reversible Hydrogels Containing Biologically Active Species, M. Durrani, Polymers in Medicine III, Elsevier Science Publishers B.V., Amsterdam, 1988, pp. 161–167.
"The Acetylation of Insulin", Lindsay et al, Biochem. J. 121 (1971), p. 737.
"Tryptase from Rat Skin: Purification and Properties", Braganza et al, Biochemistry, vol. 30, No. 20 (1991), pp. 4997–5007.
"Intramolecular Cross–Linked Insulin", D.G. Lindsay, Mar. 1971.
"Improvement of Large Intestinal Absorption of Insulin by Chemical Modification with Palmitic Acid in Rats", Hashizume et al, J. Pharm. Pharmacol. 1992, 44: 557–558.
"Trials of Lipid Modification of Peptide Hormones for Intestinal Delivery", Muranishi et al, Journal of Controlled Release, 19 (1992), pp. 179–180.
"Hypoglycemic Effect of Intestinally Administered Monosaccharide–Modified Insulin Derivatives in Rats", Haga et al, Chem. Pharm. Bull. 39(7) 1983–1986(1990), p. 1983 & p. 1986.
"Effect of Trypsin Inhibitor on Passage of Insulin Across the Intestinal Barrier", Science, 127, 1988, pp. 1115–116.

*Primary Examiner*—Edward J. Webman
*Attorney, Agent, or Firm*—Nestor W. Shust; Hudak & Shunk Co., L.P.A.

[57] ABSTRACT

A therapeutic-containing composition adapted for the oral administration of a biologically active material which comprises a water insoluble but water swellable polymer chemically modified with an enzyme inhibitor containing a chemical functionality which has an interactive affinity for target receptors located on the transport barrier walls of the digestive tract of the intended recipient, and at least one therapeutic of low oral bioavailability.

69 Claims, No Drawings

PROTEIN-CONTAINING POLYMER COMPOSITION FOR ORAL ADMINISTRATION

RELATED APPLICATIONS

This application is a continuation-in-part of U.S. patent application Ser. No. 08/408,076, filed Mar. 22, 1995, entitled "Insulin Containing Polymer Composition for Insulin, Peroral Administration", which claims priority of Russian application Ser. No. 94-010864/14 (009909) filed Mar. 23, 1994.

FIELD OF THE INVENTION

The invention relates to the compositions and method of oral administration of insulin and other therapeutic proteins and peptides which ordinarily are not easily delivered orally. The formulation may consist of a conventional chemical compound, a protein, a peptide, or a peptide bio-mimetic incorporated within a hydrogel whose polymer structure has been chemically modified to include a functionality which protects the therapeutic from degradation, and separately or simultaneously a functionality which interacts with the stomach or intestinal mucosa to favorably increase the probability of the therapeutic diffusing into the circulatory system. More specifically the invention deals with a therapeutic containing composition adapted for the oral administration of a biologically active material, this composition comprising a water swellable polymer chemically modified with an enzyme inhibitor and a protein, peptide, or peptide bio-mimetic, such as insulin, growth hormone, and erythropoietin, as well as other peptides whose molecular weight is in the range of 30,000 or less, for oral delivery in treating respectively various forms and degrees of diabetes, various growth hormone related diseases and various blood related diseases. Other uses specifically include the treatment of animal diseases and other biological applications involving growth hormones and related analogies and metabolites for improved dairy and/or meat production.

BACKGROUND OF THE INVENTION

Since the advent of biotechnology many protein therapeutics have been identified as having significant therapeutic benefits for many potentially serious diseases. Such diseases include cancer, heart disease, diseases of the central nervous system, diseases of the immune system, diseases of the blood and circulatory system, and many hormonally based diseases. Unfortunately, many of these medical disorders are chronic and require continuous administration of the required therapeutic.

However, the broad utilization of protein therapeutics, and many other hard to deliver therapeutics depends on the ability to easily administer them to patients in a controllable and acceptable manner. Clearly oral administration would be the most desirable method for administering such materials to patients who must take them for extended periods of time. Unfortunately, the ability to administer proteins in this fashion has never been achieved because typically proteins and peptides are easily metabolized in the stomach and intestine when introduced orally to patients. In addition to problems related to degradation, their molecular weights are typically too high to allow for significant transport across the gut wall into the circulatory system. This is true even if they can be protected from extensive degradation prior to getting to the gut wall barrier. As a result protein therapeutics can only be given by injection (typically intravenous (IV) or subcutaneous), and this has severely restricted their broad utilization for many diseases.

A typical and very important example of a potential application for an oral protein delivery technology is the treatment of diabetes. There are currently more than 50 million people around the world who suffer from one of several well known forms of diabetes. In has been known that most forms of diabetes can be treated with regular doses of insulin administered to counter the buildup of blood glucose which takes place when diabetics ingest foods. In addition to the patient acceptability problem associated the delivery of insulin by injection, there are other serious difficulties associated with providing insulin by injection. These include supplying and using the necessary syringes and other medical devices to patients who suffer from one form or another of diabetes in many parts of the world, the inappropriate time profile associated with delivery by injection, and the excessive amounts of insulin to which various organs of the body are subjected when insulin is administered in this fashion. All of these problems would be ameliorated by the development of an oral form of insulin which could be administered, and made available in the circulatory system along with food.

Because diabetes is a common disease, the properties and effects of Insulin are well known. It is a polypeptide hormone having a molecular weight of about 6000. It influences many metabolic processes in humans and other animals. For example, it increases the diffusion of glucose into living tissues as well as its use by cells in metabolic processes. It also reduces the glycogen content in the liver and increases its concentration in muscles. Insulin also increases protein synthesis rates, and affects other metabolic processes.

Indeed, an approach which would permit the direct oral delivery of proteins and peptides has been sought for many years, as it has been generally recognized that such an approach, if developed, would have important advantages and thus greatly expand the potential uses for protein and peptide therapeutics. Nevertheless, and in spite of extensive efforts to develop insulin preparations resistant to the action of digestive proteinase and capable of delivery into the blood stream through the intestinal mucosa. No such approach has been found and used for the general administration of insulin or other protein or peptide therapeutics up to now. Extensive work continues today throughout the world in spite of repeated failures. With respect to protein and peptide therapeutics produced by biotechnology, oral delivery has remained one of the major unfulfilled goals for at least the last 15 years. Unfortunately no effective method to accomplish this has yet been found, for insulin or any other protein or peptide. The invention and approaches described herein address this critical, and as yet unresolved issue, and provide a direct pathway to the potential practical development of an oral delivery methodology for proteins and peptides, and other hard to deliver therapeutics.

Unfortunately, the principle effective method accepted for administering insulin to diabetic patients is still via subcutaneous (SQ) and intramuscular (IM injection of a preparation containing insulin. Dosage amounts, and administration profiles vary widely from patient to patient, depending on many factors such as body weight and size, the nature of the specific form and severity of diabetes in each patient, and the degree of diet control which can be exercised by each patient. It is not possible to identify a single dosage composition or amount which can be considered a standard human dosage form. Typically such treatments must be tailored for each patient to produce a given biologic and therapeutic profile and injections must be repeated several times daily for most patients. The need to inject insulin repeatedly (500 to more than 1000 times per year for many patients) results in physical pain, emotional distress, and many related problems for patients who must undergo this treatment on a regular basis. For this reason many marginal patients, or patients who do not live in areas of the world where syringes and needles are not easily accessible do not receive therapy.

Indeed, the disadvantages of administration by injection of most protein therapeutics, has been one of the principle elements limiting the use of proteins, as therapeutics for chronic diseases. The same problems and limitations apply to the use of proteins in animals where multiple doses would be required to achieve the necessary biological effect, and to non-protein therapeutics which are not orally bioavailable.

The compositions and method of this invention relates to any number of potentially efficacious proteins and peptides as well as other therapeutics. The oral delivery of insulin, and growth hormones are used to illustrate the general applicability of the methodology and the formulations described. We show animal studies, formulations, and a methodology for making the formulations which permits the creation of insulin preparations resistant to the action of digestive proteinase. The use of these formulations permits the contained therapeutic protein to penetrate the intestinal mucosa and enter the circulatory system where it can manifest its therapeutic effect. We show further that therapeutic efficacy can be achieved with dosage levels of insulin which are comparable to the dosage levels commonly used in conventional therapeutic injections.

Several approaches have been proposed by others in the past to achieving the oral delivery of insulin. One such approach involves the modification of the insulin molecule itself. Another such approach involves the modification of insulin by replacing for example, the C-end residue of threonine with a more stable glycine residue. Yet another approach involves the hydrophobization of the insulin molecule and yet other such approaches involves the preparation of monosaccharide derivatives of insulin and the binding of insulin to other proteins.

However, despite the fact that in many of these attempts the modification of the insulin molecule does result in an increase in insulin resistance to the action of proteinase in vitro, or has been shown in some cases to result in prolonging its effect in the body when injected IV or IM, effective oral formulations have never been demonstrated using these methods. The goal of general oral administration of insulin (and most other peptide therapeutics and generally non-orally available biologically active agents) remains unfulfilled.

Another approach to solving this problem which recently has been reported in the literature involves administering insulin in combination with compounds increasing the penetrability of insulin through the intestinal wall. This approach is intended to facilitate the penetration of the active agent through the intestinal barrier, and into the blood stream. This approach is also potentially applicable for other proteins as well as to insulin since the primary action of the added agent is on the physiology, permeability and penetrability of the intestinal barrier. Fatty acid salts, surfactants, bile salts (cholate), chelate-forming compounds are all examples of materials which have been proposed and for which experiments have been attempted in this regard.

In principle the increased permeability of the intestinal wall induced by such added materials should contribute to an increased amount of protein reaching the blood stream in an active state. However, up to the present time, effects have been observed only with mixtures of such materials administered directly into the intestines, by-passing the esophagus and stomach. This approach (often referred to as peroral), has not shown a therapeutic effect even when high doses on insulin or other proteins and peptides are used. Even had positive therapeutic effects been observed, this form of administration is extremely difficult, and potentially uncomfortable for a human patient. It is not an acceptable answer to the generic problem of protein delivery or even the treatment of very severe diabetes. Yet another disadvantage of such formulations as have been studied in this manner are the potential long term effects of permeation enhancers on the intestines. Still another disadvantage is that such approaches are non-specific and can result in many undesirable materials and antigenic compounds normally excluded from transport (including viruses, degrading enzymes, and other toxic materials normally found in the intestine) transporting into the blood stream. Finally, it is clear that such approaches do not protect the formulation, including the therapeutic effect, from the degrading action of proteinase and/or other chemically active agents and enzymes present in the stomach and the gullet.

While one could modify such approaches to include in the formulations protective protease inhibitors, which could theoretically protect insulin to some degree, such work has not been carried out and shown to be effective in a formulation intended for conventional oral delivery. A similar (not very useful) result has been obtained when compositions containing protease inhibitors, insulin and compounds increasing the penetrability of intestinal walls were combined and administered directly to the bowels. In fact such an approach, with the long term effect of permeation enhancers on the intestinal and bowel wall functionality, could be very damaging.

One of the more common experimental approaches to creating oral forms for insulin delivery has been to place the insulin inside a protective shell which protects the active agent as it is passing through the digestive track up to its entry into the small intestine. The protective shell is designed to disintegrate in the small intestine releasing active insulin (or other agent if the approach is used with other peptides or proteins). As such, various coating polymers have been used with solubility properties tailored to permit the coating shell to dissolve within the small intestines. This can be accomplished by selecting coating formulations with enhanced solubility at pH's appropriate to the small intestine. In addition, microparticulates such as liposomes, hydrogels, nanocapsules and specifically biodegradable polymers (nanoparticles) have been investigated. However for all the work which has been addressed to this issue, there are no effective delivery systems or formulations for the oral administration of any protein, much less insulin or growth hormone.

Injectable insulin-containing compositions have also been reported (U.S. Pat. No. 5,049,545) which are comprised of insulin immobilized on a polymer (including a polymer hydrogel). The polymers used in such compositions are represented by materials such as starch, dextran, polyoxyethylene, polyvinylpyrrolidone, cross-linked collagen, non-therapeutically active proteins and derivatives thereof, and these formulations have included inhibitors of proteolytic enzymes. This approach has resulted in the insulin-containing polymers displaying an increased resistance to the effect of blood proteolytic enzymes, and has been shown to yield formulations which show an increased duration of insulin activity when administer directly into the bloodstream. However, the insulin-containing polymer compositions synthesized in this work do not show significant stability to the attack of the digestive enzymes and hence are not useful for oral delivery.

Saffran M., Kumar G. S., et al. Biochem. Soc. Trans. 1990, v.18, N. 5,P.752 have shown and reported on insulin-containing polymer compositions comprising an insulin-containing gelatin capsule coated by a copolymer of styrene with hydroxyethylmethacrylate, said polymer then being crosslinked with a divinylbenzene azo-containing derivative. On oral administration, the crosslinked copolymer is degraded by the action of microorganisms within the intestines with the release of insulin, a small amount of which is shown to penetrate the intestinal wall. However, a disadvantage of these compositions is that they show a low resistance to the action of digestive enzymes and hence only a very small amount of insulin is demonstrated to actually pass through the intestinal wall and appear as active insulin in the circulatory system. With the oral administration of the above-mentioned crosslinked polymer into rats in an amount of from 1 to 40 mg per rat (as calculated for insulin), the maximum reduction of glucose concentration in animal blood was 25% on average (from 384 mg/100 ml to 287 mg/100 ml) and was observed 3–4 hours after administration of the preparation. This is far below the desirable reduction of blood glucose due to insulin, and demonstrates the general lack of effectiveness of this approach. Also this approach has not been shown to be useful for the administration of any other protein or peptide, nor for use in treating humans.

Damge, C., J Controlled Release, 1990, V. 13. P. 233, showed that spherical nanocapsules may be produced from biodegradable polyisobutyl-2—cyanoacrylate, said nanocapsules having a diameter of from 250 to 350 nm, said nanocapsules containing insulin dispersed in a lipid phase. However, upon oral administration of these nanocapsules, very little effect on blood glucose was observed when normal therapeutic levels of insulin were contained within them. A measurable (though not very great) reduction in glucose concentration of only 25% was observed even when very high insulin doses were used compared to generally accepted therapeutic doses. Indeed the doses used in this study were in the range of 100 U/kg (almost 20 times higher than doses typically injected into humans to achieve therapeutic efficacy). Even more significant from a therapeutic standpoint, the insulin in this demonstration was shown to be measurably active 6 days after the capsules were administered to the host animal. Such results throw into serious question the significance of the experiments since there is no therapeutically acceptable mechanism by which the delivered protein could remain the intestine of the test animals for such a period of time undigested and unmodified (complete elimination being typically effected in 12–24 hours). Even if there were an adequate explanation for these results, such a dosage level, as well as the delivery and therapeutic profile associated with this approach, is considered to be unacceptable for insulin, and indeed for most protein therapeutics whose administration and therapeutic effect must follow closely one upon the other. In particular for insulin it is desirable for this hormone to move across the intestinal wall and enter the circulatory system along with the absorbed nutrients from food which may be ingested by the host. Such a profile is clearly not associated with the work reported by Damge.

Greenley R. Z., Broun T. M. et al. Polymer Prepr., 1990, v. 31, N 2. P.182. have reported a composition which is similar in some aspects to the compositions claimed herein. In their composition insulin is immobilized within the volume of a crosslinked polymer modified with an inhibitor of proteolytic enzymes. The crosslinked polymer is substantially a polyacrylic or polymethacrylic acid polymer crosslinked with triethyleneglycoldi(meth)acrylate. The inhibitor is an aprotinin-protease inhibitor. A disadvantage of this composition is that the synthesized polymer hydrogels have little resistance to the action of digestive enzymes. As in the other studies reported above, this limitation results in a low measured activity of insulin passing through the intestinal wall and entering the circulatory system. It would certainly result in a similar limitation with respect to other proteins and peptides contained therein. Thus, when such a modified insulin formulation of the type described by Greenly et.al. was administered to rabbits in amounts corresponding to 50 IU/Kg, the concentration of glucose in the blood is reduced after 30 min from 380 to 360 mg/100 ml. After 300 min blood glucose is shown to reach 460 mg/100 ml (no therapeutic effect). In the same study the oral administration of an unmodified hydrogel with no inhibitor (containing 50 units of insulin) was accompanied by approximately a 23% reduction in blood glucose (from 310 to 240 mg/100 ml after 300 min). At the same time the subcutaneous injection of the rabbits with only 0.23 units of insulin leads to a reduction of blood glucose concentration from 330 to 120 mg/100 ml (insulin is reduced by 74%) 150 min after the injection. Again this experiment demonstrates the limited effectiveness in animal tests of formulations intended for oral administration of insulin and other similar proteins and peptides. It should be emphasized that even were such approaches successful. Indeed, the results reported by Greenley et. al. indicate that the oral formulation described in this study is somewhere between 200 to 600 times less effective on a dosage basis than normally injected insulin, and the therapeutic usage of such a dosage form would require that massive doses of insulin be fed to patients to achieve any therapeutic effect. This is not feasible from either a practical or an economic standpoint, even if the effects were in fact shown to extend to human patients, which is not the case in this study. The study further shows that simply administering a hydrogel-like material containing an enzyme inhibitor is not sufficient to cause therapeutic amounts of insulin or proteins to pass the intestinal barrier, and that the formulations of the invention described below are distinct in their nature and effect from those tested in the past.

SUMMARY OF THE INVENTION

It is a general object of the invention to provide a composition for oral administration of therapeutic and bioactive materials whose oral availability is sufficiently limited under normal circumstances that they cannot be effectively utilized with this route of administration. More specifically, this invention deals with a composition comprising a hydrophilic polymer chemically modified with an enzyme inhibitor and a therapeutical material, often a protein or peptide, said composition being adequate for oral administration.

A further object of the invention is to provide a therapeutic-containing composition for oral administration which contains a water swellable polymer modified with an enzyme inhibitor and a therapeutic material, protein or peptide, said composition being in a tablet or capsule form, typically such that it may safely pass through the gastric environment and release the therapeutic ingredient in the small intestines.

A still further object of the invention is to increase the resistance of protein or peptide therapeutics to the effects of various digestive enzymes so as to enable such therapeutics to be more effectively administered orally.

A further object of the invention is to increase the interaction of the therapeutic-containing polymer hydrogels with selected transport barriers, and interactive sites of the intestine and/or bowels to increase the efficacy of the therapeutic substances.

A further object of the invention is to physically incorporate and entrap within the chemically modified hydrogels a protein or a peptide or other hard to deliver therapeutics without reacting, binding or substantially modifying such therapeutics, to properly protect them from premature decomposition, degradation, modification or destruction prior to its delivery to the desired location in the body such as to the intestinal barrier.

A further object of the invention is to deliver a therapeutically useful amount of a therapeutic, bioactive, or biomimetic, protein or a peptide to the target location in humans or animals to achieve useful therapeutic effects at such dosing levels that may produce desirable results similar to those when such therapeutic materials are injected into the body and/or at levels significantly lower than would be required when the therapeutics are given orally in the absence of the invention.

A further specific object of the invention is to provide an insulin containing polymer composition which is chemically modified by an enzyme inhibitor, such composition being contained within in a protective coating or capsule such that the resulting tablet or capsule may be administered orally to produce therapeutically useful effects equivalent or similar to those produced when insulin is injected subcutaneously or intramuscularly, and/or at levels much lower than would be required if insulin were to be given orally in the absence of the invention.

These and other objects are achieved by compositions and methods more specifically described below.

DETAILED DISCLOSURE OF THE INVENTION

The invention is directed to a therapeutic-containing composition adapted for the oral administration of a biologically active material which comprises:

a) a water insoluble but water swellable polymer chemically modified with a chemical agent which reduces the degradation or deactivation of therapeutics by protecting them from chemical agents ordinarily degrading to them, and containing bound to its integral structure a chemical functionality which enhances the interaction of the therapeutic containing matrix with the transport barrier walls of the digestive track or otherwise increases the proximity of the therapeutic containing formulation to the transport barrier walls so as to increase the amount which may transport into the blood stream, and b) at least one therapeutic of low oral bioavailability. More specifically, the invention is directed to a therapeutic-containing composition adapted for the oral administration of a biologically active material which comprises:

a) a water insoluble but water swellable polymer chemically modified with at least one enzyme inhibitor at least one of which contains a chemical functionality which has interactive affinity for target receptors located on the transport barrier walls of the digestive track of the intended recipient, and b) at least one therapeutic of low oral bioavailability.

More specifically, this invention is directed to a therapeutically effective composition which may be administered orally. Such compositions contain a water insoluble but water swellable polymer in the form of a hydrogel which is chemically modified with an inhibitor of enzymes or other agents, which degrade or inactivate the therapeutic materials. Such compositions also contain one or more entrapped therapeutic materials as proteins or peptides. The compositions of this invention when administered orally exhibit at least 25% of the biological efficacy of the delivered therapeutic compared to the efficacy when the therapeutic is administered by either intravenous or subcutaneous injection.

The polymers useful in this invention are desirably water interactive and/or hydrophilic in nature and are of a molecular weight or structures or have been modified such that they absorb significant quantities of water and may form hydrogels when placed in contact with water or aqueous media for a period of time sufficient to reach equilibrium with water, but which do not fully dissolve at equilibrium in water. For the purpose of specificity, we shall define a hydrogel of the invention as a polymer matrix which, when placed in contact with excess water, absorbs at least two times its weight of water at equilibrium when exposed to water at room temperature.

Such polymers should preferably be stable themselves and form stable hydrogels in a range of pH conditions ranging from pH 1 to pH 10 and most preferably be stable under pH conditions ranging from at least 3 to 9 without additional protective coatings. However, the particularly desirable stability properties must be tailored to the site of required delivery, and there may be specific times at which higher or lower stabilities to a particular pH and chemical or biological environment will be most desirable. Thus, there may be situations where susceptibility to degradation at a selected pH or in the presence of a specific hydrolytic enzyme or other degrading agent may be useful in achieving a particular delivery profile. Therefore, the formulation of the invention must be stable under conditions varying from those of the stomach to those of the site of delivery for a period of at least 2 times the normal transport time to the site of delivery in the host animal for which the therapeutic or bioactive material is intended.

The polymers of the invention may preferably include polymers from the group of homo- and copolymers based on various combinations of the following vinyl monomers: acrylic and methacrylic acids, acrylamide, methacrylamide, hydroxyethylacrylate or methacrylate, vinylpyrrolidones, as well as polyvinylalcohol and its co- and terpolymers, polyvinylacetate, its co- and terpolymers with the above listed monomers and 2-acrylamido-2-methyl-propanesulfonic acid (AMPS®). Very useful are copolymers of the above listed monomers with copolymerizable functional monomers such as acryl or methacryl amide acrylate or methacrylate esters where the ester groups are derived from straight or branched chain alkyl, aryl having up to four aromatic rings which may contain alkyl substituents of 1 to 6 carbons; steroidal, sulfates, phosphates or cationic monomers such as N,N-dimethylaminoalkyl(meth)acrylamide, dimethylaminoalkyl(meth)acrylate, (meth)acryloxyalkyltrimethylammonium chloride, (meth)acryloxyalkyldimethylbenzyl ammonium chloride. Further useful polymers are those classified as dextrans, dextrins, and from the class of materials classified as natural gums and resins, or from the class of natural polymers such as processed collagen, chitin, chitosan, pullalan, zooglan, alginates and modified alginates such as "Kelcoloid" (a polypropylene glycol modified alginate) gellan gums such as "Kelocogel", Xanathan gums such as "Keltrol", estastin, alpha hydroxy butyrate and its copolymers, hyaluronic acid and its derivatives, polylactic and glycolic acids and their derivatives and the like including chemically and physically modified versions of these polymers, gums and resins, and blends of these materials with each other or other polymers so long as the alterations, modifications or blending do not cause the final properties to fall below the minimum set for water absorption, hydrogel formation and the chemical stability required for useful application. Also polymers such as nylon, acrylan or other normally hydrophobic synthetic polymers may be sufficiently modified by reaction to become water swellable and/or form stable gels in aqueous media. In such modified form such polymers also may be acceptable for the oral delivery of some proteins if the formulations for which they are the matrix follow the other teachings of the invention.

A very useful class of polymers applicable in this invention are the carboxylic monomers are the olefinically-unsaturated carboxylic acids containing at least one activated carbon-to-carbon olefinic double bond, and at least one carboxyl group; that is, an acid or function readily converted to an acid containing an olefinic double bond which readily functions in polymerization because of its presence in the monomer molecule, either in the alpha-beta position with respect to a carboxyl group, —C=C—COOH; or as part of a terminal methylene grouping, $CH_2$=C<. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule. Maleic anhydride and other acid anhydrides useful herein have the general structure

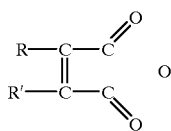

wherein R and R' are selected from the group consisting of hydrogen, halogen and cyanogen (—C≡N) groups and alkyl, aryl, alkaryl, aralkyl, and cycloalkyl groups such as methyl, ethyl, propyl, octyl, decyl, phenyl, tolyl, xylyl, benzyl, cyclohexyl, and the like.

The preferred carboxylic monomers are the monoolefinic acrylic acids having the general structure

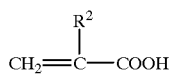

wherein $R^2$ is a substituent selected from the class consisting of hydrogen, halogen, and the cyanogen (—C≡N) groups, monovalent alkyl radicals, monovalent aryl radicals, monovalent aralkyl radicals, monovalent alkaryl radicals and monovalent cycloaliphatic radicals. Of this class, acrylic and methacrylic acid are most preferred. Other useful carboxylic monomers are maleic acid and its anhydride.

The polymers include both homopolymers of carboxylic acids or anhydrides thereof, or the defined carboxylic acids copolymerized with one or more other vinylidene monomers containing at least one terminal >$CH_2$ group. The other vinylidene monomers are present in an amount of less than 30 weight percent based upon the weight of the carboxylic acid or anhydride plus the vinylidene monomer(s). Such monomers include, for example, acrylate ester monomers including those acrylic acid ester monomers such as derivatives of an acrylic acid represented by the formula

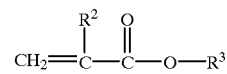

wherein $R^3$ is an alkyl group having from 1 to 30 carbon atoms, preferably 1 to 20 carbon atoms and $R^2$ is hydrogen, methyl or ethyl, present in the copolymer in amount, for example, from about 1 to 40 weight percent or more. Representative acrylates include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate and methacrylate versions thereof. Mixtures of two or three or more long chain acrylic esters may be successfully polymerized with one of the carboxylic monomers. Other comonomers include olefins, including alpha olefins, vinyl ethers, vinyl esters, and mixtures thereof.

Other vinylidene monomers may also be used, including the acrylic nitriles. The useful α,β-olefinically unsaturated nitriles are preferably the monoolefinically unsaturated nitriles having from 3 to 10 carbon atoms such as acrylonitrile, methacrylonitrile, and the like. Most preferred are acrylonitrile and methacrylonitrile. The amounts used may vary, but for some polymers are, for example from about 1 to 30 weight percent of the total monomers copolymerized. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha,beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like. Still further useful materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chlorostyrene; vinyl and allyl ethers and ketones such as vinyl methyl ether and methyl vinyl ketone; chloroacrylates; cyanoalkyl acrylates such as α-cyanomethyl acrylate, and the α-, β-, and γ-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, methylene-bisacrylamide, allylpentaerythritol, and the like; and bis (β-haloalkyl) alkenyl phosphonates such as bis(β-chloroethyl) vinyl phosphonate and the like as are known to those skilled in the art. Copolymers wherein the carboxy containing monomer is a minor constituent, and the other vinylidene monomers present as major components are readily prepared in accordance with the process of this invention.

Most preferably the hydrogels of the invention should be composed of synthetic copolymers from the group of acrylic and methacrylic acids, acrylamide, methacrylamide, hydroxyethylacrylate (HEA) or methacrylate (HEMA), and vinylpyrrolidones which are water interactive and swellable. Specific illustrative examples of useful polymers, especially for the delivery of insulin or growth hormones, are the following types of polymers:

(meth)acrylamide and 0.1 to 99 wt. % (meth)acrylic acid;
(meth)acrylamides and 0.1–75 wt % (meth)acryloxyethyl trimethyammonium chloride;
(meth)acrylamide and 0.1–75 wt % (meth)acrylamide; acrylic acid and 0.1–75 wt % alkyl(meth)acrylates;
(meth)acrylamide and 0.1–75 wt % AMPS® (trademark of Lubrizol Corp.);
(meth)acrylamide and 0 to 30 wt % alkyl(meth) acrylamides and 0.1–75 wt % AMPS®;
(meth)acrylamide and 0.1–99 wt. % HEMA;
(metb)acrylamide and 0.1 to 75 wt % HEMA and 0.1 to 99%(meth)acrylic acid;
(meth)acrylic acid and 0.1–99 wt % HEMA;
50 mole % vinyl ether and 50 mole % maleic anhydride;
(meth)acrylamide and 0.1 to 75 wt % (meth)acryloxyalky dimethyl benzylammonium chloride;
(meth)acrylamide and 0.1 to 99 wt % vinyl pyrrolidone;
(meth)acrylamide and 50 wt % vinyl pyrrolidone and 0.1–99.9 wt % (meth)acrylic acid;
(meth)acrylic acid and 0.1 to 75 wt % AMPS® and 0.1–75 wt % alkyl(meth)acrylamide. In the above examples, alkyl means $C_1$ to $C_{30}$, preferably $C_1$ to $C_{22}$, linear and branched and $C_4$ to $C_{16}$ cyclic; where (meth) is used, it means that the monomers with and without the methyl group are included. Other very useful polymers are swellable, but insoluble versions of poly(vinyl pyrrolidone) starch, carboxymethyl cellulose and polyvinyl alcohol.

Polymeric materials useful for the present purpose include (poly) hydroxyalkyl (meth)acrylate: anionic and cationic hydrogels: poly(electrolyte) complexes; Poly(vinyl alcohol) having a low acetate residual: a swellable mixture of crosslinked agar and crosslinked carboxymethyl cellulose: a swellable composition comprising methyl cellulose mixed with a sparingly crosslinked agar; a water swellable copolymer produced by a dispersion of finely divided copolymer of maleic anhydride with styrene, ethylene, propylene, or isobutylene; a water swellable polymer of N-vinyl lactams; swellable sodium salts of carboxymethyl cellulose; and the like.

Other gelable, fluid imbibing and retaining polymers useful for forming the hydrophillic hydrogel include pectin; polysaccharides such as agar, acacia, karaya, tragacenth, algins and guar and their crosslinked versions; Acrylic acid polymers, copolymers and its salt derivatives, polyacrylamides; polymer copolymers and their salt derivatives, water swellable indene maleic anhydride polymers; starch graft copolymers; acrylate type polymers and copolymers with water absorbability of about 2 to 400 times its original weight; diesters of polyglucan; a mixture of crosslinked poly(vinyl alcohol) and poly(N-vinyl-2-pyrrolidone).

Polyoxybutylene-polyethylene block copolymer gels, carob gum, polyester gels, poly urea gels, polyether gels, polyamide gels, polyimide gels, polypeptide gels, polyamino acid gels, poly cellulosic gels, Cyanamer®, crosslinked indene-maleic anhydride acrylate polymer, polysaccharides.

Representative polymers and the combinations of monomers possessing hydrophilic properties necessary to make synthetic hydrogel polymers are known to those skilled in the art. Some representative examples are disclosed in Scott et.al Handbook of Common Polymers CRC press Cleveland Ohio (1971).

Synthetic hydrogel polymers may be made by an infinite combination of several monomers in several ratios. In this instance the properties of the final hydrogel composition of this invention is the key parameter. The hydrogel can be crosslinked and it possesses the ability to imbibe and absorb fluid and swell or expand to an enlarged equilibrium state. The hydrogel is a polymeric composition and it swells or expands absorbing at least 2 to 100 fold its weight of water. The preferred level of water absorption for such hydrogels is 2 to 500 fold its weight of water, whereas the most preferred range of water absorption is 3 to 100 times the weight of the dry polymer. Generally the optimum degree of swellability for a given hydrogel must be separately determined for different therapeutics depending upon their molecular weight, size, solubility and diffusively of each entrapped therapeutic and the specific spacing and cooperative chain motion associated with each individual polymer. For insulin immobilized within the acrylamide/acrylic acid copolymer of the invention crosslinked with ethylene N,N'-bis(acrylamide) as shown in Example 2, the swollen polymer has absorbed 10–20 times its weight of water. The polymers exhibits the ability to retain a significant fraction of imbibed fluid in the polymer molecular structure. The swellable hydrophillic polymers are also know as osmopolymers. The polymer can be of plant, animal, or synthetic origin provided that it can be crosslinked and the protease inhibitor can be functionalized in a manner where it is bound to the polymer hydrogel and cannot be separated from the polymeric hydrogel by washing.

The hydrophilic polymers useful in this invention are water insoluble but water swellable. It is convenient to refer to such water swollen polymers as hydrogels or gels. Such gels may be conveniently produced from water soluble polymer by the process of crosslinking the polymers by a suitable crosslinking agent. However, stable hydrogels may also be formed from specific polymers under defined conditions of pH, temperature and/or ionic concentration. It is required for this invention that a hydrogel stable under physiologically useful conditions be formed, regardless of the means by which its stability is achieved. Preferably the polymers are cross-linked, that is, cross-linked to the extent that the polymers possess good hydrophilic properties, have improved physical integrity (as compared to the non cross-linked polymers of the same or similar type) and exhibit improved ability to retain within the gel network both the enzyme inhibitor and the therapeutic material or materials, while retaining the ability to release the therapeutic material at the appropriate location and time.

Generally the hydrogel polymers should be crosslinked with a difunctional cross-linking in the amount of from 0.01 to 25 weight percent, based on the weight of the monomers forming the copolymer, and more preferably from 0.1 to 20 weight percent and more often from 0. 1 to 15 weight percent of the crosslinking agent. Another useful amount of a crosslinking agent is 0.1 to 10 weight percent. Tri, tetra or higher multifunctional crosslinking agents may also be employed. When such reagents are utilized, lower amounts may be required to attain equivalent crosslinking density, i.e., the degree of crosslinking, or network properties which are sufficient to contain effectively the proteonase inhibitor.

The crosslinks can be covalent, ionic or hydrogen bonds with the polymer possessing the ability to swell in the presence of water containing fluids. Such crosslinkers and crosslinking reactions are known to those skilled in the art and in many cases are dependent upon the polymer system. Thus a crosslinked network may be formed by free radical copolymerization of unsaturated monomers. Polymeric hydrogels may also be formed by crosslinking preformed polymers by reacting functional groups found on the polymers such as alcohols, acids, amines with such groups as glyoxal, formaldehyde or glutaraldehyde, bis anhydrides and the like.

The polymers also may be cross-linked with any polyene, e.g. decadiene or trivinyl cyclohexane; acrylamides, such as N,N-methylene-bis (acrylamide); polyfunctional acrylates, such as trimethylol propane triacrylate; or polyfunctional vinylidene monomer containing at least 2 terminal $CH_2<$ groups, including, for example, divinyl benzene, divinyl naphthlene, allyl acrylates and the like. Particularly useful cross-linking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. They are made by the etherification of a polyhydric alcohol containing at least 2 carbon atoms and at least 2 hydroxyl groups. Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Analysis reveals the average number of ether groupings on each molecule. Efficiency of the polyether cross-linking agent increases with the number of potentially polymerizable groups on the molecule. It is preferred to utilize polyethers containing an average of two or more alkenyl ether groupings per molecule. Other cross-linking monomers include for example, diallyl esters, dimethallyl ethers, allyl or methallyl acrylates and acrylamides, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide excellent polymers. When the cross-linking agent is present, the polymeric mixtures usually contain up to about 5% or more by weight of cross-linking monomer based on the total of carboxylic acid monomer, plus other monomers, if present, and more preferably about 0.01 to 20 weight percent. A preferred crosslinking agent is alkylene N,N-bis (acyl amide), especially where the alkylene group is methylene or ethylene.

A critically important component in the composition of this invention is an enzyme inhibitor. It is generally well known that digestive enzymes which are found in the digestive tract, especially in the small intestines, rather quickly decompose proteins and peptides. Thus even if a therapeutically active protein or peptide is enclosed in a protective capsule or tablet which passes through the stomach unaffected and disintegrates in the intestines to release the therapeutically active ingredient, once that therapeutic is released it is immediately subject to the decomposing action of digestive (typically proteolytic) decomposed enzymes. The result is that after a relatively short period of time, such as even 30 minutes, there may be little of the therapeutic ingredient left in the intestines. It is precisely by this process that a protein is digested and decomposed into inactive lower molecular weight components which provide nourishment. The bound inhibitor of proteolytic enzymes incorporated in the composition of this invention helps to protect the therapeutically active protein or peptide from the action of the proteolytic enzyme and increases the probability that a therapeutic will be absorbed by the mucosa of the intestines. It is due at least partially to the action of proteolytic enzymes that when insulin is delivered through the stomach into the intestines it is relatively quickly digested and, therefore, cannot be effectively absorbed into the bloodstream.

Any inhibitor which inhibits the activity of proteolytic enzymes may be usefully employed in the composition and the delivery system for proteins and peptides. Useful inhibitors include soybean trypsin inhibitor, pancreatic trypsin inhibitor, chymotrypsin inhibitor and trypsin and chrymotrypsin inhibitor isolated from potato (solanum tuberosum L.) tubers (see Isolation and characterization of a novel trypsin and chymotrypsin inhibitor from potato tubers. Revina, T. A.; Valueva, T. A.; Ermolova, N. V.; Kladnitskaya, G. V.; Mosolov, V. V. A. N. Balh Inst. Biochem., Russian Academy Sci., Moscow, 117071, Russia. Biokhimiya (Moscow) (1995), 60(11), 1844–52. CODEN: BIOHAO; ISSN: 0320–9725. Journal written in Russian. CAN 124:49041). A combination or mixtures of inhibitors may be employed.

The most preferred and desirable inhibitor of said proteolytic enzymes is an ovomucoid-enzyme which may be isolated from the white of duck eggs, turkey eggs (chicken eggs or the eggs other fowl) (cf. USSR Inventor's Certificate N 1404513, IPC C07 K 3/02.B.I. I 23 1988), or which may be obtained by conventional biosynthesis, separation and purification approaches, genetic engineering, or other appropriate methodologies which permit the enzyme to be isolated, collected, and purified. The most preferred inhibitor is the ovomucoid enzyme isolated from the white of the duck eggs. Other inhibitors and hydrogel functionalizing agents may be appropriate for protecting enzymes from other mechanisms of degradation depending upon the specific protein used, its susceptibility to degradation under specific conditions, and the target barrier for transmission into the circulatory system.

Protecting a bioactive protein from the action of the proteolytic enzymes by the use of appropriate inhibitors is a critically important feature of this invention. Thus it is important that the protective agent be retained within the structure of the hydrogel. This is why one critical aspect of the invention involves the binding by chemical means of the inhibitor to the hydrogel. This effect is illustrated in the subsequent examples. The inhibitor may also be immobilized through sufficient physical entrapment within the polymer matrix. However, by itself even this would not result in a truly successful and effective delivery system. It is further necessary to increase the association of the protein or peptide-containing polymer hydrogel with selected transport barriers of the intestine and/or bowels to facilitate access and transport of the therapeutic substances through the barriers and into the circulatory system. This may be accomplished by incorporating into the composition (and the delivery system) of this invention a functional agent such as, but not limited to, a glycoside, a sugar containing molecule or a binding agent such as a lectin binding agent which is known to interact with the desired intestinal transport barrier. Again, it is necessary that this associative agent or functionality be bound to the hydrogel. In this manner the hydrogel preferably attaches itself to the intestinal walls and facilitates the passage of the therapeutic protein or peptide into the circulatory system. If the associative agent is not bound, it may easily diffuse away from the formulation and its effect will be lost. This effect is also illustrated in the subsequent examples.

The functional agents such as glycosides may be chemically incorporated into the polymeric hydrogel. Examples of such glycosides are glucosides, fructosides, galactosides, arabinosides, mannosides and their alkyl substituted derivatives and natural glycosides such as arbutin, phlorizin, amygdalin, digitonin, saponin, and indican. There are several ways in which a typical glycoside may be bound to polymer. For example, the hydrogen of the hydroxyl groups of a glycoside or other similar carbohydrate may be replaced by the alkyl group from the hydrogel to form an ether. Also, the hydroxyl groups of the glycosides may be reacted to esterify the carboxyl groups of the polymeric hydrogel to form polymeric esters in situ. Another approach would be to employ condensation of acetobromoglucose with cholest-5-en-3.beta.-ol on a copolymer of maleic acid. N-substituted polyacrylamides can be synthesized by the reaction of activated polymers with omega-aminoalkylglycosides: (1) (carbohydrate-spacer)(n)-polyacrylamide, 'pseudopolysaccharides'; (2) (carbohydrate spacer)(n)-phosphatidylethanolamine(m)-polyacrylamide, neoglycolipids, derivatives of phosphatidylethanolamine; (3) (carbohydrate-spacer)(n)-biotin(m)-polyacrylamide. These biotinylated derivatives may attach to lectins on the gut wall and facilitate absorption of encapsulated proteins and peptides.

Glycoproteins having N,N'-diacetylchitobiose and N-acetyllactosamine can be synthesized on the basis of radical copolymerization of n-pentenylated derivatives with acrylamides (see Macromolecules (1991), 24(15), 4236–51 and On Tai Leung et al New J. Chem (1994), 18(3), 349–63).

It is possible and indeed most preferable that the proteolytic enzyme inhibitor also contain the associative binding agent. For this reason ovomucoid which is a specific example of a class of glycoproteins, is the most preferred proteolytic enzyme inhibitor. It has a molecular weight of about 31000. The amino-acid composition of the protein portion of ovomucoid is given in Table I. A molecule of ovomucoid comprises 12.5% by weight of glucosamine and 7.8% by weight of other sugars. It is known that the villi and other structures of the intestine mucosa contain lectin (sugar) bearing receptors. Hence, the presence of lectin-like groups attached to the gel matrix is a useful aspect of the invention. While the gel material may be separately functionalized to contain lectin-like functionality and an enzyme inhibitor, a bound ovomucoid molecule incorporates both functionalities and, as may be seen from the examples, gives optimal enhancement for the delivery of incorporated insulin. Of the various ovomucoids which may be utilized, ovomucoid from duck eggs contains 3 active centers which may bind a wide variety of enzymes. It is the most preferred ovomucoid. Ovomucoid derived from chicken and turkey eggs have fewer binding centers. When a lectin containing enzyme inhibitor is used for the delivery of insulin, it is preferred that in the protective enzyme inhibitor the sugar content should be at least 3%, although a lower content may be acceptable for some applications and the delivery of some therapeutics under certain circumstances. It is an important though not limiting aspect of the invention that the enzyme inhibitor, whether ovomucoid or some other glycoprotein serving a similar function, contains both an interactive functionality for the target transport barrier, and the chemical and conformational characteristics necessary to protect the therapeutic protein with which it is closely intermixed; and/or associated within the hydrogel. It is further taught and is an important aspect of the invention that the binding functionality whether a lectin binding agent or some other agent, may be separately incorporated and functionalized into the polymer of the hydrogel, the protective enzyme inhibitor then being separately bound or immobilized to the polymeric matrix material.

The amount of the inhibitor, that is, the proteolytic enzyme inhibitor containing also a lectin binding agent, that needs to be incorporated in the composition of this invention will vary depending on (a) the specific inhibitor (e.g., the source of the ovomucoid, such as from the duck eggs, turkey eggs, chicken eggs or eggs of other fowl or from potato tubers), (b) the number of functional groups present in the molecule which may be reacted to introduce ethylenic unsaturation necessary for copolymerization with the hydrogel forming monomers, and (c) the number of lectin groups, such as glycosides, which are present in the inhibitor molecule. It may also depend on the specific therapeutic protein which is intended to be introduced into the circulatory system. Generally speaking, the amount should be sufficient to provide the desired proteolytic enzyme inhibiting function (protection of the therapeutic) and the desired binding action with the intestinal receptors. It may be necessary to conduct some routine tests to determine the optimum amount but this would be evident to those skilled in the art.

A useful amount of an ovomucoid is from 0.1 mg. per ml. of gel to 50 mg. per ml. of gel and preferable from 0.2 mg. per ml. of gel to 25 mg. per ml. of gel. The above preferred range is especially applicable when ovomucoid isolated from the duck eggs is used. This lower limit was determined from the observation that if it is used in an amount of less than 0.2 mg per ml of gel, and especially 0.1 mg, the insulin is not measurably protected from degradation and to a large extent insulin is destroyed by proteolytic enzymes. The upper limit useful for ovomucoid incorporation is based on the observation that addition of ovomucoid in an amount greater than 25 mg per ml of gel, and especially 50 mg., does not measurably increase the efficacy of the administered insulin. However, use of ovomucoid in an amount greater than 25 mg. per ml of gel causes no particular harm, and may provide greater shelf life or long term stability of the preformulated materials. In addition, larger concentrations of ovomucoid may provide added benefit in terms of longer term release of some materials.

When the inhibitor function and the binding action function are incorporated or bound to the polymer hydrogel separately (i.e., they are not part of the same molecule as is in the case of an ovomucoid), the amount of each ingredient that must be bound to the polymer will be determined in a similar manner as described above.

Ovomucoid is representative and the most important proteolytic enzyme inhibitor of the invention. Ovomucoid isolated from duck egg white is a glycoprotein containing 12.5% glucosamine (21.6 mole per mole protein) and 7.8% other sugars, giving a reaction with phenol sulphuric acid.

The molecular mass of the ovomucoid determined by the light-scattering method is 30 900±400, close to the values calculated from amino acid analysis and carbohydrate composition (31 500) and determined by polyacrylamide gel electrophoresis in the presence of sodium dodecyl sulphate and β-mercaptoethanol (30 500±1000). Its composition is given in Table 1.

TABLE 1

AMINO-ACID CONTENT OF
OVOMUCOID FROM DUCK EGG WHITE

| AMINO ACID | RESIDUES PER MOLECULE |
|---|---|
| Asp | 30.14 (30) |
| Thr | 17.98 (18) |
| Ser | 12.98 (13) |
| Glu | 23.63 (24) |
| Pro | 10.24 (10) |
| Gly | 19.75 (20) |
| Ala | 10.45 (10) |
| 1/2 CYS | 13.56 (14) |

TABLE 1-continued

AMINO-ACID CONTENT OF OVOMUCOID FROM DUCK EGG WHITE

| AMINO ACID | RESIDUES PER MOLECULE | |
|---|---|---|
| Val | 14.77 | (15) |
| Met | 6.32 | (6) |
| Ile | 3.59 | (2) |
| Leu | 12.76 | (13) |
| Tyr | 9.53 | (10) |
| Phe | 5.00 | (5) |
| Lys | 16.36 | (16) |
| His | 4.23 | (4) |
| Arg | 1.95 | (2) |
| Trp | 0 | |
| Total | | (212) |
| $M_r$ Residues | 25,178.0 | |

For the composition of this invention to be effective as an oral delivery system for the therapeutic proteins and peptides, it is necessary to prepare the composition in a particular way and not simply admix the necessary ingredients. As noted above, one important function of the proteolytic enzyme inhibitor is to protect the protein or the peptide from decomposition by the enzyme. Ovomucoid is known to be an inhibitor of proteolysis, but if a protein and ovomucoid are simply admixed and, for example, placed into water, both will diffuse and ovomucoid will not be able to protect the protein from degradation. Such formulations will not be useful as interactive delivery systems to deliver a therapeutic across the intestinal barrier. Thus an important aspect of this invention is the specific combination of the proteolytic enzyme inhibitor, and a binding agent with a polymeric hydrogel. This is accomplished by chemically modifying the polymer hydrogel with a material which contains both a proteolytic inhibitor and a binding agent (e.g., ovomucoid) immobilizing the inhibitor and the binding agent by making it part of the crosslinked polymer network. It is also possible to chemically modify the gel separately with an interactive agent such as a glycosidal containing molecule, and a nonglycosidal containing proteolytic enzyme inhibitor.

Generally speaking, first the inhibitor is functionalized, that is, an appropriate reactive group is chemically added to the inhibitor, most often an ethylenic polymerizable group is added, and the functionalized inhibitor is then copolymerized with monomers and a crosslinking agent using a standard polymerization method such as solution polymerization (usually in water), emulsion, suspension or dispersion polymerization. More specifically, the functionalization agent should have a high enough concentration of functional or polymerizable groups to insure that several sites on the inhibitor are functionalized. For example, in ovomucoid there are thirteen amine sites which may be functionalized and it is preferred for this invention that at least five of such sites are functionalized. After functionalization, the functionalized inhibitor is mixed with the monomers and a crosslinking agent which comprise the reagents from which the polymer gel is formed. Polymerization is then induced in this medium to create a polymeric gel containing the bound inhibitor. The gel is then washed with water or other appropriate solvents and otherwise purified to remove trace unreacted impurities and, if necessary, ground or broken up by physical means such as by stirring, forcing it through a mesh, ultrasonication or other suitable means to the preferred particle size. The solvent, usually water, is then removed in such a manner as to not denature the inhibitor. The preferred method is lyophillization (freeze drying) but other methods are available and may be used (e.g., vacuum drying, air drying, spray drying, etc.). A more detailed description of the above described method is given in Example 3.

In functionalizing the inhibitor protein the object is to introduce a functional group onto the surface of the inhibitor protein that can subsequently react in polymerization or otherwise couple the inhibitor protein to the hydrogel. As examples of introducing polymerizable groups one may react available amino, hydroxyl and thiol groups from the protein inhibitor, with electrophiles containing unsaturated groups. For example, unsaturated monomers containing N-hydroxy succinimidyl groups, active carbonates such as p-nitrophenyl carbonate, trichlorophenyl carbonates, tresylate, oxycarbonylimidazoles, epoxide, isocyanates and aldehyde, and unsaturated carboxymethyl azides and unsaturated orthopyridyl-disulfide belong to this category of reagents. Illustrative examples of unsaturated reagents are ally glycidyl ether, allyl chloride, allylbromide, allyl iodide, acryloyl chloride, allyl isocyanate, allylsulfonyl chloride, maleic anhydride, copolymers of maleic anhydride and allyl ether and the like.

All of the lysine active derivatives, except aldehyde, can generally react with other amino acids such as imidazole groups of histidine and hydroxyl groups of tyrosine and the thiol groups of cystine if the local environment enhances nucleophilicity of these groups. Aldehyde containing functionalizing reagents are specific to lysine. These types of reactions with available groups from lysines, cystines, tyrosine have been extensively documented in the literature and are known to those skilled in the art.

In the case of ovomucoid which contains amine groups, it is convenient to react such groups with an acyloyl chloride, such as acryloyl chloride, and introduce the polymerizable acrylic group onto the ovomucoid. Then during the preparation of the polymeric hydrogel, such as during the crosslinking of the copolymer of acrylamide and acrylic acid, the functionalized ovomucoid, through the acrylic groups, is attached to the polymer and becomes bound thereto.

The therapeutic ingredients which may be administered orally employing the delivery system and the compositions of this invention are proteins and peptides including monopeptides, dipeptides, tripeptides, and polypeptides. Also may be administered orally proteins which are modified to act as carriers for biologically active materials, including anti-sense oligonucleotides, genes and viral vector drug carriers and many conventional organic compounds of low stability, solubility and consequently low oral bioavailability.

Illustrative examples of therapeutic proteins are nucleoprotein, glycoprotein, lipoprotein, immunotherapeutic, porcine somatotropin for increasing feed conversion efficiency in a pig, insulin, growth hormone, buserelin, leuprolide, metoclopramide, fentanyl, lidocaine, ketoprofen, sufentainil, terbutaline, droperidol, interferon, scopolamine, testosterone, gonadorelin, ciclopirox, olamine, buspirone, calcitonin, cromolyn sodium or midazolam, and other bioactive proteins and recombinant protein products.

Illustrative examples of peptides are cyclosporin, lisinopril, captopril, delapril, cimetidine, ranitidine, famotidine (Pepcid), tissue plasminogen activator, epidermal growth factor, fibroblast growth factor (acidic or basic), platelet derived growth factor, transforming growth factor (alpha or beta), vasoactive intestinal peptide, tumor necrosis factor; hormones such as glucagon, calcitonin, adrecosticotrophic hormone, aldoetecone, follicle stimulating hormone, enkaphalins, β-endorphin, somatostin, gonadotrophine, α-melanocyte stimulating hormone. Additional examples are bombesin, atrial naturiuretic peptides and luteinizing hormone releasing (LHRH), substance P, vasopressin, α-globulins, transferrin, fibrinogen, β-lipoproteins, β-globulins, prothrombin (bovine), ceruloplasmin, $\alpha_2$-glycoproteins, $\alpha_2$-globulins, fetuin (bovine), $\alpha_1$-lipoproteins, $\alpha_1$-globulins, albumin and prealbumin.

Other therapeutics of normally low bioavailability, such as nucleic acids, may be administered orally to human or animal subjects. Table 7 contains a more complete though not inclusive listing of therapeutics which may be administered orally employing the composition and method of the invention.

Insulin utilized in the invention can be any of the natural or synthetic insulins known in the art, many of which are commercially available. Some such insulins may themselves be modified and/or formulated to alter their delivery profile and availability. The use of several or a mixture of these different forms of insulin in the formulations of the invention may be advantageous in designing tailored therapeutic profiles for patients, as may a change in the crosslink density of the gel.

The growth hormones which may be delivered orally using the invention may be commercially available human growth hormone, bovine growth hormone, porcine growth hormone, or other representative animal growth hormone extracted from natural sources, or produced via genetic engineering and related production fermentation methodologies which are well known and described in the art of protein and peptide manufacture.

Proteins that may be administered orally employing the composition of this invention should be of molecular weight less than 1,000,000 daltons, and preferably less than 65,000. More preferably the molecular weight of proteins should be less than 32,500 and especially less than 10,000 daltons. Usually they have molecular weight of at least 300 daltons.

Other therapeutics which may be most advantageously delivered orally utilizing this invention should generally be of molecular weight greater than 100 daltons, although many of them will be at least 500 daltons, be unstable to pH conditions in the stomach, intestine, and/or bowel, be subject to degradation or inactivation by enzymes or other chemicals present in the digestive tract and have limited water solubility, and/or have a limited transport rate across the mucosal barriers of the stomach, intestine, and/or bowel, such that their bioavailability when delivered orally is less than 30% of the total ingested. Any therapeutic or biologically active molecule regardless of molecular weight which has some limited water solubility, but cannot be transported across the various barriers of the digestive track in therapeutically sufficient amounts incorporated into a formulation otherwise meeting the criteria of the invention may be considered a therapeutic for the purpose of this invention regardless of its chemical designation, source, or reason for low bioavailability.

The composition of this invention, that is, a composition adopted for the oral administration of proteins or peptides comprising a polymeric hydrogel which, preferably, has been crosslinked, and which has been modified by a proteolytic enzyme inhibitor and a binding agent, and contains a protein or a peptide, may be administered in a gel form. Generally any desired dose may be administered to a human or an animal. The dose actually delivered can be calculated based on the amount of the biologically active therapeutic material contained in a unit weight or volume of the gel. However, when a gel containing non-bound therapeutic is introduced to the stomach which contains no free therapeutic there is a kinetic driving force which must result in rapid loss of the therapeutic from the gel. For example, insulin containing hydrogel placed in a pH adjusted saline loses 90% of its contained insulin in 15 minutes. Unless rapid and reproducible dumping of the stomach contents into the intestine can be assured, variable, and unreliable dosages will be delivered from patient to patient, and from one administration to the next, making controllable therapeutic and biological effects difficult to assure.

It is, therefore, more convenient and preferred to administer the therapeutic containing composition of this invention in tablet form or gel capsules as is well known to the art. When administered in that form then the tablet or gel capsule is enterically coated. The enteric coating assures that the therapeutic-containing composition passes into the intestinal tract without being significantly affected or partially degraded in the stomach, regardless of the time profile of delivery to the intestine. In the intestinal tract the coating dissolves and the composition functions as described above.

Enteric coating materials useful in the present invention include those coating materials resistant to degradation in the stomach but which will decompose in the environment of the intestinal tract to expose the coated material. Such enteric coating materials include, but are not limited to, the following ingredients either singly or in combination: hydroxypropyl methylcellulose phthalate, polyethylene glycol-6000, and shellac, and they may be dissolved in solvents including dichloromethane, ethanol and water, cellulose phthalate, or polyvinyl acetate phthalate.

A useful enteric coating material for coating insulin comprises 4.5 parts by weight hydroxymethylcellulose to 0.5 parts shellac, to 0.5 parts polyethylene glycol-6000. This material is dissolved in 47.3 parts dichloromethane and 37.8 parts ethanol. The enteric coating material is then diluted with water to an optimal concentration and is applied to the compositions of the invention.

Many other coating materials useful for pharmaceutical preparations are well known and available in the industry. They include conversion products of polysuccinimide as disclosed in U.S. Pat. No. 5,175,285; acrylic polymers such as those derived from lower alkyl esters of acrylic and methacrylic acids which may be copolymerized with other copolymerizable monomers, such as those containing carboxyl or quaternary ammonium groups and/or with acrylic or methacrylic acid as described in U.S. Pat. No. 5,422,121 and U.S. Pat. No. 4,644,031.

Other well known ingredients may also be incorporated. Examples are binder materials, such as various types of cellulose and their derivatives, providone and polyethylene glycol fatty acid ester groups; fillers, such as gum acacia, crystalline cellulose, hydroxypropylcellulose and hydroxypropyl-methylcellulose; surfactant materials, such as cationic anionic or nonionic surfactants illustrated by sodium lauryl sulfate, stearyl amine, polyglycerine fatty acid esters and many other fatty acid esters; emulsifying agents, such as cholesterol, stearic, palmic and oleic acids and their sodium salts, various stearates and polysorbates (20, 40, 60, 80) propylene glycol diacetate and the like; and antimicrobiol agents, such as methylparaben, ethylparaben, propylparaben, butylparaben, phenol, dehydroacetic acid, phenylethyl alcohol, sodium benzoate, sorbic acid, thymol, thimerosal, sodium dehydroacetate, benzyl alcohol, butylparaben, cresol, p-chloro-m-cresol, chlorobutanol, phenylmercuric acetate, phenylmercuric borate, phenylmercuric nitrate and benzalkonium chloride.

The invention will be further understood and illustrated, without limiting it, by referring to the following examples.

EXAMPLE 1

Isolation of Ovomucoid

To a flask equipped with a stirrer was added 100 g of egg white. Next 100 g of a mixture comprised of 70 g of ethyl alcohol, 30 g of a solution comprised of 2.7 g trichloracetic acid and 27.3 g of distilled water was added to the flask at a rate of from 3 to 5 ml/min while stirring. Upon addition of the entire amount of the specified mixture the reaction mass was further stirred for 40 min. at a temperature which may range between 15 and 25° C. The precipitate was filtered, and removed from the remaining solution. This precipitate was then rejected having no further value. The filtrate from this step was then transferred to a second flask and mixed with 550 g of ethyl alcohol. The precipitate from this latter step was then dialyzed using distilled water and then dried by lyophilization. The yield from this procedure was about 0.8 g of ovomucoid.

The above procedure is specific to the isolation of ovomucoid from duck eggs. However, the same procedure may be used to obtain ovomucoid from other sources using the egg white of other fowl, or other protein and glycoprotein containing sources replacing the 100 gm of egg white used in step one above. More or less ovomucoid may be obtained depending on the source material, and the variability of ovomucoid in the source material. In addition, the conditions of extraction and precipitation may be varied in temperature and time, and the quantities of solvents may also be varied to optimize the extraction of ovomucoid from different materials.

EXAMPLE 2

Functionalization of Ovomucoid

In a 20 ml beaker, 10 ml of a $NaCO_3$ buffer solution at pH 8 was stirred. Isolated ovomucoid (100 mg) was added and dissolved with agitation. Acryloyl chloride (10 m) was added to this solution at room temperature and stirred until the reaction was complete.

EXAMPLE 3

Preparation of Polymer

To the solution obtained in Example 2 was added acrylamide (1 g) and N,N-methylene-bis (acrylamide) (0.1 gm). (When commercial grade acrylamide is used it contains up to about 1.5% of acrylic acid), 10 mg. of $(NH_4)_2S_2O_8$ and 10 $\mu$l of TMEDA (tetramethylethylene diamine) were added to initiate polymerization. The reaction mixture was stirred to insure good mixing but stopped just before the cloud point of polymerization. The resulting gel was screened through a nylon mesh. The particles were washed with $NaCO_3$ buffer solution and then lyophylized until dry.

EXAMPLE 4

General Procedure for Preparing Orally Active Insulin Composition

For insulin therapeutics a representative composition is prepared in the following manner: 0.01–1.0 g of a pre-dried 4.5% cross-linked polymer modified with 0.2–25 mg of ovomucoid is placed in 0.3–3.0 ml of insulin solution (conveniently in a saline solution) with insulin being at a concentration of 0.01 to 3 mg/ml of liquid (insulin activity may range from 0.25–100 I.U./ml for 1 hour at room temperature. During this time the polymer swells completely, imbibing the insulin containing solution, and reaching equilibrium and is ready for use. This methodology for preparation is not limited to the specific time given, and may be judiciously varied over a range of times and temperatures depending on a number of variables such as the crosslink density of the polymer, the temperature under which the exposure of hydrogel is carried out. The polymer may also be exposed to larger or smaller amounts of insulin concentration, and or amounts of fluid, and of course the total amount of material processed may be increased or decreased by changing the amount of insulin containing solution and hydrogel is used in the process.

Following are the polymers used in Examples 5 to 24 as reported in Tables 2 to 5. These crosslinked hydrogel polymers were prepared according to the procedure of Example 3.

PAA—polyacrylamide

PMA—polymethacrylamide

PHEMA—polyhydroxyethylmethacrylate

PVP—polyvinylpyrrolidone

PAAC—polyacrylic acid

EXAMPLES 5–15k

General Procedure for Preparing and Administering Oral Formulation of Insulin

The polymer used in these Examples was prepared according to Example 3 using the crosslinking agent in the amount of 0.5% of the initial monomer solution. 0.1 g of a pre-dried crosslinked polyacrylamide polymer (containing possibly up to 3% by weight of acrylic acid) modified with ovomucoid (isolated from the white of duck eggs except when indicated otherwise) is placed in an excess of aqueous insulin solution, the insulin activity of the solution being 25 I.U./mg, the insulin concentration of said solution being 1.0 mg/ml of the saline solution at room temperature. The polymer is exposed to the solution for a period of 1 hour. After this period of time the imbibing of the insulin containing solution reaches equilibrium and the polymer has swollen completely. The polymers that show a measurable effect will have absorbed at least 0.5 g of aqueous solution of insulin. The formulation was removed from the insulin solution and was ready for use.

The insulin containing hydrogel was administered orally to non-diabetic rabbits, using a catheter, in an amount corresponding to 5 I.U. of insulin per kg of animal weight. It was administered in the form of a swollen hydrogel which passes through the stomach very quickly (10–20 min. depending on the specific animal) and therefore does not result in substantial decomposition/hydrolysis of insulin. Blood samples were collected after 30, 60, 90 and 120 minutes. In Example 15 the procedure described above was followed, except that the hydrogel polymer was not modified with an ovomucoid.

In Table 2 for each Example the various columns show the concentration of insulin in the saline solution, the specific modified polymer used, the amount of dry polymer (g.) per ml of the swollen gel, the ovomucoid concentration (g.) per ml of swollen modified polymer and the glucose level in blood at the indicated time, i.e., minutes after administration. The column identified as "Polymer Conc. (g./ml)" shows the degree of water absorbed by the polymer. Water absorption is inversely proportional to the density of the polymer in the resulting gel. Thus a polymer which absorbs 10 mg. of water per ml. of the resulting gel will have a polymer concentration of approximately 0.1.

It may be clearly seen from these examples that the oral administration of insulin using the composition of this invention where the polymer hydrogel was modified with bound ovomucoid, over a wide range of insulin and ovomucoid loading levels, always results in a measurable and physiologically meaningful decrease in blood sugar in the test animals. Example 15k, which may be considered a control exam, shows that when the polymer is not modified, the insulin in the formulation has no effect on the blood level in the rabbit.

TABLE 2

INSULIN IN MODIFIED POLYMER ADMINISTERED ORALLY TO NON-DIABETIC RABBITS

| Example Number | Insulin[a] Solution Conc. mg/ml gel | Modified Polymer | Polymer Conc. (g/ml) | Ovomucoid Conc. mg/ml of Gel | Glucose Conc. in Blood mg/100 ml ± 8% Minutes After Administration | | | | |
|---|---|---|---|---|---|---|---|---|---|
| | | | | | T = 0 | T = 30 | T = 60 | T = 90 | T = 120 |
| 5 | 1.0 | PAA | 0.1 | 8.0 | 150 | 132 | 110 | 80 | 80 |
| 6 | 3.0 | PAA | 0.05 | 7.7 | 150 | 110 | 95 | 90 | 80 |
| 7 | 1.0 | PAA | 0.01 | 0.2 | 140 | 100 | 95 | 90 | 80 |
| 8 | 5.0 | PAA | 0.1 | 25.0 | 120 | 90 | 80 | 80 | 90 |
| 9 | 0.91 | PMA | 0.1 | 13.1 | 160 | 125 | 95 | 90 | 120 |
| 10 | 0.05 | PHEMA | 1.0 | 3.8 | 120 | 110 | 90 | 90 | 110 |
| 11 | 0.08 | PVP | 0.3 | 8.1 | 110 | 90 | 70 | 90 | 90 |
| 12 | 3.0 | PAAC | 0.1 | 7.4 | 160 | 145 | 100 | 90 | 100 |
| 13 | 1.0 | PAA | 0.2 | 7.4[b] | 140 | 110 | 90 | 90 | 110 |
| 14 | 2.0 | PAA | 0.3 | 7.4 | 120 | 90 | 80 | 80 | 90 |
| 15k | 1.0 | PAA | 0.1 | NM[c] | 160 | 160 | 158 | 160 | — |

Table Notations:
[a] The following insulins were used: Examples 5–9, 14 and 15 - porcine; Examples 12–13 - cattle; Examples 10–11 - human.
[b] Ovomucoid was isolated from the white of turkey eggs
[c] NM - the polymer was not modified with the ovomucoid

EXAMPLES 16–18

Experimental diabetes was induced in white rats (Wistar line—weighing about 180 grams each) by way of intraperitoneal administered streptozotocin administered to the rats at a dosing level of 70 mg/kg of weight. Insulin containing polymeric formulations administered to the rats after their glucose level was determined to exceed 400 mg %. The results are shown in Table 3. A physiological reduction of glucose in these induced diabetic rats was seen for these examples (polymer used was modified with ovomucoid inhibitor). When compared to the insulin injection control shown in Example 18k, the results in Examples 16 and 17 are quite startling in that the effect of the same dosage of insulin injected in Example 18k was only slightly greater than the effect of the oral dosage form.

EXAMPLES 19k–22k

Control Experiments

Non-diabetic rabbits were treated orally with an insulin saline solution in an amount of 7 I.U./kg animal weight (Example 19), a mixture of ovomucoid (2.5 mg/kg weight), and insulin solution (8 I.U./kg) (Example 20) and modified hydrogel (200 mg/kg weight) (Example 20). The results are shown in Table 4 and it is clear that none of these ingredients above or in the indicated combination have any effect on the glucose level in the blood of the rabbits. This is consistent with all expectations based on the past literature and the scientific work in the field. The "Prototype" reported in Example 22k are the results published in R. Z. Greenly, T. M. Brown, J. Garbow, C. E. Vogt, H. Zia, R. L. Rodgers, M. Christie and L. A. Luzzi, Polymer Matrices for Oral Delivery, Polymer Preprints, V. 31, N 2, p. 182–183, 1990.

TABLE 3

INSULIN IN MODIFIED POLYMER ADMINISTERED ORALLY TO DIABETIC RATS

| Example Number | Insulin[a] Solution Conc. mg/ml gel | Modified Polymer | Polymer Conc. (gm/ml) | Ovomucoid Conc. mg/ml of Gel | Animal Type - Method of Administration | Glucose Conc. in Blood mg/100 ml ± 8% Minutes After Administration | | | |
|---|---|---|---|---|---|---|---|---|---|
| | | | | | | T = 0 | T = 30 | T = 60 | T = 90 |
| 16 | 1.0 | PAA | 0.1 | 7.4 | Rat-Oral | 500 | 300 | 250 | 250 |
| 17 | 3.0 | PAA | 0.1 | 7.4 | Rat-Oral | 800 | 450 | 450 | 500 |
| 18k | — | 12 I.U./kg Insulin Solution | — | — | Rat-Subcutaneous | 400 | 160 | 145 | 150 |

Table Notations:
[a] Porcine insulin 12 I.U./kg

TABLE 4

CONTROL EXPERIMENTS

| Example Number | Material Administered (Amount) | Animal Type - Method of Administration | Glucose Conc. in Blood mg/100 ml ± 8% Minutes After Adimnistration | | | | |
|---|---|---|---|---|---|---|---|
| | | | T = 0 | T = 30 | T = 60 | T = 90 | T = 120 |
| 19k | Insulin Solution | Rabbit - Oral | 152 | 151 | 150 | 160 | — |
| 20k | Mixture of Ovomucoid and Insulin | Rabbit - Oral | 154 | 154 | 155 | 153 | — |
| 21k | Modified PAA | Rabbit - Oral | 153 | 152 | 154 | 154 | — |
| 22k | Prototype | Rabbit - Oral | 380 | 360 | 430 | 410 | 420 |

EXAMPLES 23-24

ORAL GROWTH HORMONE DELIVERY

An unmodified polyacrylamide (PAA) gel sample is caused to imbibe approximately 100 counts of Radioactive labeled growth hormone intermixed with a normal therapeutic dosage of growth hormone (10 μg/kg). The methodology for absorption is as given in Example 5 except that a mixture of radiolabelled and normal human growth hormone is substituted for the insulin. The sample counts are determined and the sample is administered orally to rats as a control (Example 23). No count of growth hormone is observed in the blood by radioimmunoassay after 2 hours. Another sample of PAA modified with ovomucoid as described in Example 3 is similarly treated, measured and administered. Approximately one hundred counts are determined to be present in the sample prior to administration. After 2 hours, approximately 25 counts can be measured as having passed through the intestinal barrier and entered the circulatory system using the same radioimmunoassay techniques as used in Example 23. The results are shown in Table

EXAMPLE 25

The protective effect of ovomucoid on proteins ranging in molecular weight from 16,000 to well in excess of 300,000 is shown in Table 6. In the experiments reported in Table 6, trypsin, a lytic enzyme, was incorporated in the indicated molar ratio with the protein to simulate the physiological condition in the intestinal tract where a lytic enzyme initiates the hydrolysis of the protein. It can clearly be seen that a very small quantity of the inhibitor can protect a large amount of protein (in excess of 300 times its molar amount) against lytic degradation. It is easily seen that while more than 90 percent of the protein remains undegraded in the presence of a protective inhibitor, less than one percent is found to remain after only 2 hours when no ovomucoid inhibitor is present. The effect of incorporating ovomucoid is to enhance the active protein present at physiologically meaningful times by a factor of more than 10, and for many of the materials studied by approximately 100 or more over the two hour period following ingestion.

TABLE 5

ORAL ADMINISTRATION OF HUMAN GROWTH HORMONE TO RATS

| Example Number | Mg HGH per ml Gel | Polymer | Polymer Concentration (g/ml) | Ovomucoid Conc. mg/ml of Gel | Radioactive Count After 120 Min. |
|---|---|---|---|---|---|
| 23k | 1.0 | PAA | ~0.1 | NM[c] | 0 |
| 24k | 1.0 | PAA | ~0.1 | 7.4 | ~25 |

Table Notations and Abbreviations:
(c) NM - the polymer was not modified with any inhibitor It is clearly seen from data in Tables 2 to 5 that the formulations of the claimed invention, that is, where an inhibitor of proteolytic enzymes was chemically bonded to the polymer matrix, have the ability to prevent insulin degradation in the gastrointestinal tract and enables the passage of significantly efficacious quantities of insulin into the host animals bloodstream. Insulin activity displayed for the claimed compositions is shown to be 60% to 70% of the activity obtained when the same dosage of insulin was administered by injection.

TABLE 6

PROTECTIVE EFFECT OF OVOMUCOID[a]

| Protein | Molecular Weight | Molar Ratio Protein/ Enzyme | Ovomucoid Inhibitor (mg) | Degradation at 2 Hr, 25° C. in Water |
|---|---|---|---|---|
| Myoglobin | 17,000 | 300/1 | 1.0 mg | 4–5% |
| Myoglobin | 17,000 | 300/1 | 0.0 mg | >99% |
| Ovalbumin | 43,000 | 300/1 | 1.0 mg | 4–5% |
| Ovalbumin | 43,000 | 300/1 | 0.0 mg | >99% |
| Senim Albumin | 69,000 | 300/1 | 1.0 mg | 6–7% |
| Sertim Albumin | 69,000 | 300/1 | 0.0 mg | >99% |

TABLE 6-continued

PROTECTIVE EFFECT OF OVOMUCOID[a]

| Protein | Molecular Weight | Molar Ratio Protein/ Enzyme | Ovomucoid Inhibitor (mg) | Degradation at 2 Hr, 25° C. in Water |
|---|---|---|---|---|
| Fibrinogen | 340,000 | 300/1 | 1.0 mg | 6–7% |
| Fibrinogen | 340,000 | 300/1 | 0.0 mg | >99% |

[a]The lytic enzyme is Trypsin
The amount of Trypsin 0.5 mg (a) The lytic enzyme is Typsin The amount of Trypsin 0.5 mg with non-bound ovomucoid [for the resistant stomach capsule] again had no effect (experiments d and e) [even at the highest insulin level in either a stomach resistant capsule or a polyacrylamide gel].

However, when the ovomucoid inhibitor was bound to the polymeric gel (as in experiments f and g) substantial lowering of glucose was observed, even at 4–6 times lower insulin dosage levels than were used in experiments a–e.

TABLE 7

EFFECT OF ORAL ADMINISTRATION OF INSULIN IN CAPSULES TO RABBITS WITH BOUND AND NON-BOUND OVOMUCOID INHIBITOR

| | Formulation Content/Dose | Blood Glucose Concentration mg/100 ml. | | | | |
|---|---|---|---|---|---|---|
| | | Time = 0 min. | Time = 30 min. | Time = 60 min. | Time = 90 min | OTEI at 90 min. |
| a | 15 mg ovomucoid + 62 I.U./kg insulin in stomach-resistant capsule | 140 ± 8 | 140 ± 8 | 130 ± 8 | 130 ± 8 | <0.02 |
| b | 15 mg ovomucoid + 62 I.U./kg insulin in stomach-resistant capsule | 120 ± 7 | 100 ± 6 | 100 ± 6 | 120 ± 7 | <0.02 |
| c | 15 mg ovomucoid + 37 I.U./kg insulin in stomach-resistant capsule | 120 ± 7 | 120 ± 7 | 130 ± 7 | — | <0.02 |
| d | polyacrylamide gel with 10.0 mg of non-bound ovomucoid and 63 I.U./kg insulin in stomach resistant capsule | 100 ± 6 | 90 ± 6 | 100 ± 6 | 140 ± 8 | <0.02 |
| e | polyacrylamide gel with 10.0 mg of non-bound ovomucoid and 63 I.U./kg insulin in stomach resistant capsule | 100 ± 6 | #OO ± 6 | 140 ± 8 | — | <0.02 |
| f | polyacrylamide gel with 10.0 mg of bound ovomucoid and 10.0 I.U./kg insulin in stomach resistant capsule | 120 ± 7 | 80 ± 5 | 60 ± 4 | 50 ± 3 | ~0.7 |
| g | polyacrylamide gel with 10.0 mg of bound ovomucoid and 7.0 I.U./kg insulin in stomach resistant capsule | 130 ± 7 | 100 ± 6 | 100 ± 6 | 50 ± 5 | ~1.0 |

EXAMPLE 26

This example demonstrates THE criticality of binding the protective inhibitor of the invention to the polymeric matrix of the hydrogel. In this experiment the indicated formulation was enclosed in a stomach-resistant capsule which comprised a gelatin capsule coated with cellulose acetate/phthalate from the mixture of acetone and ethanol (9:1 by volume) solution. The indicated formulation contained in the stomach resistant capsule was administered to healthy rabbits and the concentration of glucose in the blood was determined at the indicated time intervals after administration. The results in Table 7 show that a wide range of insulin dosing yields no physiological effect in the absence of a bound inhibitor. Even loading 10 to 20 times the normal physiological dosage of insulin into a stomach resistant capsule to protect the insulin from degradation in the stomach produced no effect as indicated in experiments 4a and b. [Loading protective ovomucoid into the capsule also had no effect (4c)]. [Substituting] Including a polyacrylamide gel Using this and similar experiments as a guide, we can define a unique measure of effectiveness for an oral protein delivery formulation as follows. This measure shall be defined for the purpose of this patent as the Oral Therapeutic Efficiency Index "OTEI". The OTEI of any formulation, given orally and of the formulations of the invention described herein may be determined by applying the equation: $OTEI = OD/ND \times TE_o/TE_n$. To the results of any study where the efficacy of a therapeutic or biologically active formulation is evaluated for effect. In equation (1) OD is defined as the oral dosage of the formulation under study (per kilo of body weight) and ND is the normal human therapeutic dosage level per kilo of body weight which is usually different for each therapeutic. Typically ND for hard to deliver therapeutics is delivered by IM or IV injection as in the case of insulin and most other proteins. However it may also be given as an implanted bolus as in the case of growth hormone in some animal formulations, as an implanted device intended to release the material over a defined period of time. Such therapeutics may also be administered as an intravenous fluid drip, or as in the case of conventional pharmaceutical of low bioavailability it may even be given orally but may have to be given at very high dosing levels because it not be very efficient in being utilized by the subject. $TE_o$ in equation (1) is defined as the therapeutic effect of the oral formulation being evaluated (determined in the appropriate fashion for the pharmaceutical or animal product question). Thus for example in the case of insulin its normal therapeutic effect may be determined by measuring blood sugar, or by measuring directly the level of insulin in the blood stream. In the later case one must determine the normal levels of insulin the hepatic portal system and the peripheral circulatory system separately since they may well be different. In such cases where several different accepted indicators may be used Different OTEI's may be determined for the same formulations in the same subject. However, in such cases the overall results should be similar. Where possible it is preferred to measure directly the therapeutic effect such as blood glucose in the case of insulin administration. $TE_n$ in equation (1) is the normal therapeutic effect accepted by those skilled in the art expected from the administration Of ND. Again this is preferably determined by evaluating a direct therapeutic marker such as blood sugar is for insulin, but may be determined by measuring against a secondary marker for the presence of the therapeutic such as IGF 1 or IGF 2 as in the case of growth hormone. As in the evaluation of $TE_o$. one may also use a direct measure of the drug itself in the blood stream or any other part of the body where it is expected to exert its therapeutic effect. The crucial factor is that the same measure is used to evaluate $TE_o$ and $TE_n$ so that a true comparison of the effect and enhancement of required activity of the oral formulation may be made.

For the purpose of illustrating the impact of the formulations of the invention on protein, and particularly on insulin delivery we consider a typical normal injected dosage of insulin to a human patient or an animal test subject to be ~10 T.U./Kg of body weight. It is important to note that dosage level chosen could be greater or lower within a significant amount without changing the conclusions drawn from the examples given here, and the results published in other literature. Again, for the purpose of evaluation of the data in the examples the smallest meaningful change in glucose level which can be reliably determined in Table 7 is taken to be about 15%–20% of the value of any given measurement (smaller changes can be seen, but their causes are less clear and we choose not to include them). Hence, for the purpose of analysis of the data in examples from Tables 7–9 we ignore changes of less than 15% of the base level insulin reading for each test subject The base level is taken as the measurement for that subject at time zero in the examples given. The decrease in insulin expected for a non diabetic animal given a normal injected dosage of the same level would be very large (probably greater than 80% of the initial reading) and indeed such a dosage could be fatal to the test subject. However, for the purpose of calculating an OTEI we expect that a decrease of at least 100 units from the base level at t=0 would be expected if a normal dosage of insulin were injected. If 20 units of glucose is given as the most reasonable limit on meaningful detectable change in blood glucose due to the administration of insulin, the OTEI for the formulations evaluated in experiment (a) in Table 7 would be <0.02. (i.e <10/62×<.2). Very low OTEI's value would be determined for experiments (b)–(e) in Table 7, typical of most work to date on the oral delivery of insulin and other proteins. However, the dosage forms used in experiments (e) and (f) in Table 7 yield glucose decreases very close to what would be expected from injecting comparable levels of insulin. Using the definition of OTEI given above, and 10 U/Kg as an acceptable standard dosage level for insulin representative of human and animal dosing levels, the OTEI calculated in for experiment (f) in Table 7 would be OTEI 4f=10/10×70/90=~0.7. OTEI 4 g=10/7×60/90=~1.0

Table 7 clearly shows through evaluation of the OTEI's of the described experiments that simply administering ovomucoid and insulin or incorporating them in a hydrogel (even at much higher levels than would be normally used) does not result in physiologically significant transport and efficacy. However when hydrogels of the invention are utilized, the resultant OTEI's are enhanced by several orders of magnitude. If a lower insulin dosage (eg 3 I.U./Kg) were chosen as a standard human dosage, the absolute OTEI's would be lower (0.24 for (e) and 0.33 for (f) in Table 7). However the conclusions and comparison to other oral formulations would be the same, (i.e., that formulations of the invention show much greater delivery of an active therapeutic delivered in a normal profile than do other formulations which have been investigated for similar purposes).

In Table 8 it can be seen that the OTEI's of all the formulations which do not contain bound inhibitors of the invention are very low, and limited only by the degree of accuracy of determining changes in blood glucose in the animals. The OTEI of experiment (g), however, is reproducibly 10 to 20 times higher than any other formulation, and is within a factor of 2 to 3 of what might be expected for an injectable form of insulin in rabbits, assuming that a standard dosage would be 3 I.U./kg in such animals.

TABLE 8

EFFECT OF ORAL ADMINISTRATION OF SELECTED INSULIN FORMULATIONS IN RABBITS

| | Formulation Content/Dose | Blood Glucose Concentration mg/100 ml. | | | | OTEI at 90 min. |
|---|---|---|---|---|---|---|
| | | Time = 0 | Time = 30 min. | Time = 60 min. | Time = 90 min. | |
| a | Insulin[a], 3 I.U./kg | 152 | 152 | 159 | 150 | <1 |
| b | Insulin[a], 6 I.U./kg | 152 | 151 | 150 | 160 | <.05 |
| c | Ovomucoid, 2.5 mg/kg + insulin[a], 8 I.U/kg | 154 115 | 154 115 | 155 120 | 153 — | <.04 |
| d | Unmodified hydrogel + insulin[a], 8 I.U./kg | 160 | 160 | 158 | 160 | <.04 |
| e | Unmodified hydrogel + insulin[a], 11 I.U./kg + Ovomucoid, 4 mg/kg | 175 160 | 175 160 | 160 150 | 157 — | <.025 <.025 |
| f | Hydrogel modified by inhibitors (without sugar functionality)[b] + insulin[a], 10 I.U./kg | 120 | — | 120 | 120 | <.04 |
| g | Hydrogel modified by ovomucoid | 150 | 132 | 110 | 80 | ~0.4 |

TABLE 8-continued

EFFECT OF ORAL ADMINISTRATION OF SELECTED INSULIN FORMULATIONS IN RABBITS

| | Blood Glucose Concentration mg/100 ml. | | | | |
|---|---|---|---|---|---|
| Formulation Content/Dose | Time = 0 | Time = 30 min. | Time = 60 min. | Time = 90 min. | OTEI at 90 min. |
| (with sugar functionality) + | 150 | 110 | 95 | 90 | ~0.35 |
| insulin[a], 5 I.U./kg | 160 | 125 | 95 | 90 | ~0.4 |

[a]Saline solution of insulin used normally for human ingestion.
[b]Ovomucoid without polysaccharide functions; the saccharide functions were hydrolyzed with the enzyme amylase in water at pH of 7–8

Table 9 shows that formulations in which the lectin binding group is separately bound to the gel formulation are also effective in delivering insulin to the blood stream. While the effect is somewhat less than is observed when the lectin binding group is attached directly to the enzyme inhibitor as in ovomucoid, the formulations are still remarkably active and yield results far in excess of any reported to date with respect to oral delivery of proteins.

TABLE 9

Alternative Insulin Formulations Administered Orally to Non-Diabetic Rabbits

| Formulation* Administered (dose of insulin 8 U/kg) in 1 ml. of swollen Hydrogel | Glucose Concentration in the Blood mg/100 ml Minutes After Administration | | | | |
|---|---|---|---|---|---|
| | 0 | 30 | 60 | 90 | 120 |
| Control 1 Nothing Administered (without insulin) | 145 | 145 | 150 | 160 | 160 |
| Control 2 (subcutaneous insulin) | 105 | 60 | 55 | 60 | 65 |
| N1 | 145 | 145 | 145 | 150 | 160 |
| N2 | 120 | 95 | 90 | 95 | 95 |
| N3 | 140 | 120 | 110 | 110 | 110 |
| N4 | 120 | 115 | 120 | 120 | 125 |
| N5 | 150 | 140 | 120 | 130 | 130 |
| N6 | 160 | 150 | 130 | 135 | 140 |

Notes on formulations in Table 9:

*N 1. The polymer matrix was obtained by copolymerization of unsaturated (functionalized derivative of trypsin inhibitor with acryloyl chloride as in Example 2) from soy bean with acrylamide and N,N'-methylene-bis-(acrylamide) (concentration of inhibitor 5 mg/ml swollen hydrogel). Trypsin inhibitor from soy bean protein can inhibit the activity of trypsin (not chymotrypsin and other proteinases).

N 2. Polyacrylamide hydrogel modified with trypsin inhibitor from soy bean (5 mg/ml swollen hydrogel) and dextran (Molecular Mass (MM) 70000, concentration 2 mg/ml swollen hydrogel). Immobilization of inhibitor and dextran was carried out by oxidation of dextran with sodium periodate, interaction of resulting dialdehyde dextran with sodium borohydride, acylation of aminogroups of inhibitor with acryloyl chloride and copolymerization of unsaturated derivative of inhibitor and dextran with acrylamide and N,N'-methylene-bis-(acrylamide).

N 3. Obtained by copolymerization of unsaturated derivative of trypsin inhibitor from soy bean with acryloyl glucoseamine and N,N'-methylene-bis (acrylamide) (concentration of inhibitor 8 mg/ml swollen hydrogel).

N 4. Obtained by copolymerization of unsaturated derivative of trypsin inhibitor from bovine pancreas with acrylamide and N,N'-methylene-bis-(acrylamide) (concentration of inhibitor 4,5 mg/ml swollen hydrogel). Trypsin inhibitor from bovine pancreas—protein which can inhibit the activity of trypsin (not chymotrypsin and other proteinases).

N 5. Polyacrylamide hydrogel modified with trypsin inhibitor from bovine pancreas (6 mg/ml swollen hydrogel) and dextran (MM 10000, concentration 3,5-mg/ml swollen hydrogel). Immobilizataion of inhibitor and dextran was carried out in the above manner as in N 2.

N 6. Obtained by copolymerization of unsaturated derivative of chicken egg white ovomucoid with acrylamide and N,N'-methylene-bis(acrylamide) (concentration of inhibitor 5 mg/ml swollen hydrogel). Chicken egg white ovomucoid—trypsin inhibitor, glycoprotein (contains polysaccharide) which can inhibit the activity of trypsin only (not chymotrypsin and other proteinases).

It was pointed out above that the protease inhibitor must be chemically bound (immobilized) to the hydrogel polymer. Another method of binding (immobilizing) the protease inhibitor into the hydrogel network is to entrap the protease inhibitor in the network via physical means rather than covalent bonding. In this manner the network that is formed via crosslinking is such that the protease inhibitor is trapped within the mesh structure due to its three dimensional structure being larger than the three dimensional openings of the hydrogel network. Other methods of association such as hydrogen bonding, salt association, and hydrophobic association that will cause retention of the protease inhibitor within the hydrogel matrix are known to those skilled in the art and may also be employed in this invention to bind (immobilize).

Table 10 shows a long term effect (over 4 weeks) of insulin administered in a modified polymer on diabetic white rats (diabetes was induced experimentally). In the reported experiments, insulin was administered in the form of a gel which contained 200 μg. of insulin per milliliter of gel. The polymer and the insulin containing gel used were the same as described in Examples 5 to 15k. The gel was administered orally by a catheter in the amount corresponding to 5.0 I.U. per kg. of animal weight.

TABLE 10

EFFECT OF INSULIN IN MODIFIED POLYMER ADMINISTERED ORALLY TO DIABETIC RATS

| Exper. | Initial Level[a] | After 1 Week | After 2 Weeks | After 3 Weeks | After 4 Weeks | Remarks |
|---|---|---|---|---|---|---|
| a | 800 | 650 | 500 | 200 | 160 | |
| b | 600 | 400 | 400 | 200 | 145 | |
| c | 400 | 350 | 180 | 100 | — | Normalized |
| d | 700 | 580 | 400 | 130 | 100 | |
| e | 760 | 500 | 140 | — | 120 | Without insulin 3rd and 4th Week |
| f | 800 | 430 | 400 | 400 | 220 | |
| g | 450 | 200 | 200 | 180 | 160 | |
| h | 500 | 280 | 300 | 200 | 200 | |
| i | 800 | 800 | 760 | 850 | 800 | Control |
| j | 700 | 800 | 750 | — | — | Died |
| k | 120 | 100 | 130 | 120 | 140 | |

Glucose Conc. in Blends mg/100 ml. I 8%

[a] Daily at 200 μg./ml insulin in 1 ml of gel (a) Daily at 200 μg./ml insulin in 1 ml of gel Further illustrative examples of therapeutic or physiologically active materials which have relatively low bioavailability when administered to a human or an animal are listed in Tables 11 and 12 below. These physiologically active materials may be conveniently administered employing the delivery system and thus the method of this invention. The bioavailability of these materials are increased when they are administered using the method of this invention.

TABLE 11a

THERAPEUTICS OF LOW ORAL BIOAVAILABILITY

| THERAPEUTIC | Oral Avail. (%) | TRERAPEUTIC | Oral Avail. (%) |
|---|---|---|---|
| Acyclovir | 15–30 | Ethosuximide | |
| Alfentanil | | Fentanyl | |
| Alprazolam | | Flurazepam | |
| Alprenolol | 8.6 | Gentamicin | |
| Amikacin | | Gold Sodium Thiomalate | |
| Amphoterican B | | Heparin | |
| Altracurium | | Hydralazine | 16 |
| Azlocillin | | Kanamycin | |
| Bleomycin | | Labetalol | 20 |
| Busulfan | | Lorcainide (dose dependent) | |
| Carbenicillin | | Methicillin | |
| Carmustine | | Methohexital | |
| Cefamandole | | Methyldopa | 25 |
| Cefazolin | | Mezlocillin | |
| Cefonicid | | Naloxone | 2 |
| Cefoperazone | | Neostigmine | |
| Ceforanide | | Netilmicin | |
| Cefotaxime | | Nicotine | |
| Cefoxitin | | Pancuronium | |
| Ceftazidime | | Piperacillin | |
| Ceftizoxime | | Prazepam | |
| Ceftiroxime | | Pyridostigmine | 14 |
| Cephalothin | | Quinine | |
| Cephapirin | | Rifampin | |
| Chlorambucil | | Streptomycin | |
| Chlorothiazide (dose dependent) | 1 g  9  50 mg  56 | Terbutaline | 15 |
| Cisplatin | | Thiopental | |
| Clorazepate | | Ticarcillin | |
| Cocaine | 0.5 | Tobramycin | |
| Cytarabine | 20 | Tubocurarine | |

TABLE 11a-continued

| Doxorubicin | | Vancomycin | |
|---|---|---|---|
| Edrophonium | | | |

(Goodman & Gillmans The Pharmacological Basis of Therapeutics*, Hardman, J. G. (ed) & Limbird, L. E. (ed) Ninth Edition (1996) McGraw-Hill, New York)

| THERAPEUTIC | Oral Avail. (%) | TRERAPEUTIC | Oral Avail. (%) |
|---|---|---|---|
| Aldesleukin | | Lincomycin | 20–30 |
| Alteplase (t-PA) | | Lisinopril | 25 |
| Amiloride | | Lovastatin | |
| Anistreplase | | Mercaptopurine (administered with allopurinol) | 12  60 |
| Auranofin | 15–25 | Morphine | 24 |
| Aztreonam | <1 | Moxalactam | 3 |
| Bretylium | 23 | Nalbuphine | 16 |
| Bromocriptine | 3–6 | Naltrexone | 5–40 |
| Budesonide | 12 | Nicardipine | 18 |
| Nasel | 21 | | |
| Bupivacaine | | Nimodipine | 10 |
| Bupropion | | Nitrendipine | 11 |
| Capreomycin | | Nitroglycerine Sublingual Topical | <1  38  72 |
| Carboplatin | | Octreotide SubQ Intranasal | <2  100  25 |
| Carvedilol | 25 | Paclitaxel | Low |
| Cefaclor | | Pentamidine | Negligible |
| Ceftriaxone | | Pravastatin | 18 |
| Cinoxacin | | Pyridostigmine | 14 |
| Dobutamine | | Rifabutin | 20 |
| Doxorubicin | 5 | Selegiline | Negligible |
| Esmolol | | Simvastatin | <5 |
| Felodipine | 5 | Spironolactone (after IV Canrecone) | 25 |
| Flumazenil | 20 | Tacrine | 17 |
| Fluorouracil | 28 | Tacrolimus | 16 |
| Ganciclovir | 3 | Terbutaline | 14 |
| Isotretinoin | 25 | Tetrahydro-cannabinol Smoking | 4–12  2–50 |
| Isradipine | 19 | Triamcinolone Acetonide | 23 |

[a]From Goodman and Gilman's The Pharmacological Basis ofTherapeutics, 1985.

a) From Goodman and Gilman's The Pharmacological Basis of Therapeutics, 1985.

TABLE 11b

Further examples of Low Bioavailability Drugs from Cho (U.S. Pat. No. 4,849,227) not listed specifically in Table 7a or elsewhere in text.

| | |
|---|---|
| Urokinase | for treating thrombosis |
| Factor VII | for treating hemophilia |
| Leuprolid | for treating prostrate cancer |
| Gangliocides | for improving neurotransmission |
| Vincrostine | for treating cancer |
| Belomyein | for treating cancer |
| Adrinmycin | for treating cancer |
| Lidocane | for treating cardiac arrhythmia |
| Cephalosporidines | for treating infection |
| Erythromycin | |
| Bretylium Tosylate | |
| Cetiedile | |
| Cyclandelate | |
| Chloramphenicol | |

TABLE 12

Some Proteins and Peptides of Low Molecular Weight
Amenable to Oral Delivery by Compositions of the Invention

|   | Name | Molecular Weight |
|---|---|---|
| 1 | Parathyroid Hormone (PTH) (PTH-RP) | 20194 |
| 2 | Selenoprotein P (Selanoprotein P Precursor) | 42,614 |
| 3 | Cystatin B (Liver Thiol Proteinase Inhibitor) | 11,174 |
| 4 | Tumor Invasion-inhibiting Factor 2 (TIIF-2) | |
| 5 | Tat Protein of HIV-1 | 9758 |
| 6 | HIV Protease | |
| 7 | Transactivating Regulatory Protein (BPC-157) | 40,000 |
| 8 | Megakaryocyte Stimulatory Factor (MGDF) | 37822 |
| 9 | Granulocyte-macrophage Colony Stimulating Factor Precursor (GM-CSF) | 16295 |
| 10 | Soluble Epoxide Hydrolase (CEH) | 62633 |
| 11 | IL-1 Receptor Agonist (IL-1-RA) | 20,055 |
| 12 | Calcitonin | 15467 |
| 13 | Tumor Necrosis Factor (TNF) (also Catchetin) | 25644 |
| 14 | IFN Gamma (Interferon Gamma Precursor) | 19348 |
| 15 | Interleukin-1 (IL-2) (TCGF) T Cell Growth Factor | 17628 |
| 16* | Interleukin-3 (IL-3) | 17233 |
| 17 | Interleukin-4 (IL-4) (BSF-1) (B Cell Stimulatory Factor) | 17492 |
| 18 | Interleukin-7 (IL-7) | 20,128 |
| 19 | Hemopoietic Cell Growth Factors | |
| 20 | Erythropoietin (EPO-R) Erythropoietin Receptor Precursor | 55065 |
| 21 | Ovomucoids (from Duck, Chicken, Turkey and Other Fowl) | ~28,000 |
| 22** | Megainins (Synthetic and Natural) | ~1000–3000 |

*Includes role of IL-3 as a precursor, multipotential colony-stimulating factor, hemopoietic growth factor, P-cell stimulating factor and mast-cell growth factor (MCGF)
**Megainins are low molecular weight peptides which may be divided from the skin of frogs or synthesized directly. They have shown potential as antibiotics but are only useful topically because of their low oral availability.

Some Proteins and Peptides of Low Molecular
Weight Amenable to Oral Delivery by
Compositions of the Invention

*Includes role of IL-3 as a precursor, multipotential colony-stimulating factor, hemopoietic growth factor, P-cell stimulating factor and mast-cell growth factor (MCGF)
**Megainins are low molecular weight peptides which may be divided from the skin of frogs or synthesized directly. They have shown potential as antibiotics but are only useful topically because of their low oral availability.

We claim:

1. A therapeutic-containing composition adapted for the oral administration of a biologically active material comprising
   (a) a water insoluble, but water swellable, polymer which contains at least one enzyme inhibitor covalently bound to the polymer and a chemical functionality which has an interactive affinity for target receptors located on the transport barrier walls of the digestive tract of the intended human or animal specie, wherein said chemical functionality is either integral to the structure of said inhibitor or is covalently bound to the polymer and
   (b) one or more of therapeutic or biologically active agents.

2. A composition of claim 1 wherein said polymer is a gel forming hydrophilic polymer.

3. A composition of claim 2 wherein the gel forming polymer is partially crosslinked.

4. A composition of claim 3 wherein the crosslink density is about 0.01% to about 25%.

5. A composition of claim 3 wherein the crosslink density is about 0.01% to about 15%.

6. A composition of claim 2 wherein the inhibitor is an inhibitor of proteolytic enzymes.

7. A composition of claim 6 wherein the inhibitor is ovomucoid.

8. A composition of claim 7 wherein ovomucoid is functionalized by reacting ovomucoid with a polymerizable material.

9. A composition of claim 8 wherein the polymerizable material is acryloyl chloride.

10. A composition of claims 1, 4, 6, 7, or 9 wherein the polymeric hydrogel is a homopolymer or a copolymer prepared from one or more monomers selected from the group consisting of acrylic and methacrylic acids, acrylamide, methacrylamide, hydroxyethylacrylate and methacrylate, and vinylpyrrolidones, and the therapeutic is a protein or a peptide with a molecular weight of less than 100,000 daltons.

11. A composition of claim 10 wherein the protein is insulin.

12. A composition of claim 10 wherein the protein is a growth hormone or a somatotropin.

13. A composition of claim 12 wherein the protein is selected from the group consisting of human growth hormone (HGH), bovine growth hormone (BGH or BST), porcine growth hormone (PGH or PST), their analogues and derivatives and epidermal growth factor (FGF) and its analogues.

14. A composition of claim 10 wherein the protein is selected from the group consisting of interleukins, interleukin receptors and interleukin receptor agonists.

15. A composition of claim 10 wherein the protein is an interferon.

16. A composition of claim 10 wherein the protein is selected from the group consisting of blood cell growth stimulating factors and precursors and erithropoitin (EPO) and its analogues.

17. A composition of claim 10 wherein the protein is selected from the group consisting of parathyroid hormone (PTH), selenoprotein P, cystatin B and its liver thiol protease inhibitor analogues, endotoxin neutralizing protein, megakaryocyte simulatory factor (MGDF), granulocyte macrophage colony stimulating factor (GM-CSF), genofibrate, alpha calcitonin, beta calcitonin, tumor necrosis factor (TNF), tumor invasion inhibiting factors, transacting regulatory proteins (TAT's) of HIV and other retroviruses, protease inhibitors, and BPC 157, fat reducing hormones, and analogues and variants of these proteins.

18. A composition of claim 10 wherein the concentration of enzyme inhibitor is from 0.01 to 25 milligram of enzyme per gram of dry polymer.

19. A composition of claim 11 wherein the concentration of enzyme inhibitor is from 0.01 to 25 milligram of enzyme per gram of dry polymer.

20. A composition of claim 12 wherein the concentration of enzyme inhibitor is from 0.2 to 3 milligram of enzyme per gram of dry polymer.

21. The composition of claim 1 wherein the affinity functionality of the inhibitor of proteolytic enzymes is represented by lectin binding groups such as sugars or related glycosides and wherein these binding groups represent at least more than 3% of the weight of the unbound inhibitor.

22. A composition of claim 10 wherein the protein is of a molecular weight less than 65,000 daltons.

23. A composition of claims 1, 3, 4, 6, 7, 8, 9, which is enclosed within an enteric protective coating.

24. A composition of claim 23 additionally containing pharmacologically acceptable antimicrobial agents, stabilizers, salts and other formulation adjutants.

25. A composition of claim 10 wherein the inhibitor is ovomucoid.

26. A composition of matter adapted for the oral administration of insulin, said composition comprising
   (a) a polymeric hydrogel which is a homopolymer or a copolymer derived from one or more monomers selected from the group consisting of acrylic and methacrylic acids, acrylamide, methacrylamide, hydroxyethylacrylate or methacrylate, and vinylpyrrolidones; said hydrogel having been crosslinked with 5 to 20 weight percent of a crosslinking agent and said hydrogel containing in its polymer network covalently bonded ovomucoid derived from the white of the duck eggs, and
   (b) insulin.

27. A composition of claim 26, wherein the ovomucoid is functionalized prior to being covalently bonded to the polymer network.

28. A composition of claim 27 wherein the functionalizing agent is acryloyl chloride and the crosslinking agent is alkylene N,N-bis(acyl amide).

29. A composition of claim 28 wherein the polymeric hydrogel is a copolymer prepared from 40–99.5 weight percent of acrylamide and 0.5–60 weight percent of acrylic acid.

30. A composition of claim 29 wherein the polymeric hydrogel is a copolymer prepared from 40–90 weight percent of acrylamide and 10–60 weight percent of acrylic acid.

31. A composition of claim 29 wherein the polymeric hydrogel is a copolymer prepared from 95–99.5 weight percent of acrylamide and 0.5–5 weight percent of acrylic acid.

32. A composition of matter adapted for the oral administration of a growth hormone, said composition comprising
   (a) a polymeric hydrogel which is a homopolymer or a copolymer derived from one or more monomers selected from the group consisting of acrylic and methacrylic acids, acrylamide, methacrylamide, hydroxyethylacrylate or methacrylate, and vinylpyrrolidones; said hydrogel having been crosslinked with 5 to 20 weight percent of a crosslinking agent and said hydrogel containing in its polymer network covalently bonded ovomucoid derived from the white of the duck eggs, and
   (b) a growth hormone.

33. A composition of claim 32 wherein the ovomucoid is functionalized prior to being covalently bonded to the polymer network.

34. A composition of claim 33 wherein the functionalizing agent is acryloyl chloride and the crosslinking agent is alkylene N,N-bis(acyl amide).

35. A composition of claim 34 wherein the polymeric hydrogel is a copolymer prepared from 40–99.5 weight percent of acrylamide and 0.5–60 weight percent of acrylic acid.

36. A composition of claim 35 wherein the polymeric hydrogel is a copolymer prepared from 40–90 weight percent acrylamide and 10–60 weight percent of acrylic acid.

37. A composition of claim 35 wherein the polymeric hydrogel is a copolymer prepared from 95–99.5 weight percent acrylamide and 0.5–5 weight percent of acrylic acid.

38. A composition of claim 35 wherein the growth hormone is selected from the group consisting of human growth hormone, bovine growth hormone and porcine growth hormone.

39. A method of orally administering one or more biologically active materials comprising
   (a) preparing a composition for oral ingestion which contains a water insoluble, but water swellable, polymer having an enzyme inhibitor covalently bonded thereto, and a chemical functionality which has an interactive affinity for target receptors located on the transport barrier walls of the digestive tract of the intended human or animal specie, wherein said chemical functionality is either integral to the structure of said inhibitor or is covalently bound to the polymer and also containing one or more therapeutic or biologically active agents and
   (b) orally administering said composition to a human or animal specie.

40. A method of claim 39 wherein the polymer is partially crosslinked.

41. A method of claim 39 wherein the inhibitor is an inhibitor of proteolytic enzymes.

42. A method of claim 41 wherein the inhibitor is ovomucoid.

43. A method of claim 42 wherein ovomucoid is functionalized by reacting ovomucoid with a polymerizable material.

44. A method of claim 43 wherein the therapeutic is a protein.

45. A method of claim 44 wherein the protein is selected from the group consisting of insulin, a growth hormone and a somatotropin.

46. A therapeutic-containing composition adapted for the oral administration of a biologically active material comprising
   (a) a water insoluble, but water swellable, polymer which contains at least one enzyme inhibitor covalently bonded to said polymer, said inhibitor containing a chemical functionality which has an interactive affinity for target receptors located on the transport barrier walls of the digestive tract of the intended human or animal specie, and
   (b) one or more of therapeutic or biologically active agents, said composition having an oral therapeutic efficiency index (OTEI) of at least 0.05.

47. A composition of claim 46 wherein the gel forming polymer is partially crosslinked.

48. A composition of claim 47 wherein the biologically active agent is a protein.

49. A composition of claim 48 wherein the inhibitor is an inhibitor of proteolytic enzymes.

50. A composition of claim 49 wherein the inhibitor is ovomucoid.

51. A composition of claim 50 wherein ovomucoid is functionalized by reacting ovomucoid with a polymerizable material.

52. A composition of claim 51, wherein the protein is selected from the group consisting of insulin, growth hormone and a somatotropin.

53. A composition of claim 52 wherein protein is insulin and the OTEI is at least 0.1.

54. A composition of claim 53 wherein the OTEI is at least 0.5.

55. A therapeutic-containing composition adapted for the oral administration of a biologically active material comprising
   (a) a water insoluble, but water swellable, polymer containing within its matrix covalently bonded enzyme inhibitor and also containing a chemical functionality which has an interactive affinity for target receptors located on the transport barrier walls of the digestive tract of the intended human or animal specie, wherein said chemical functionality is either integral to the structure of said inhibitor or is covalently bound to the polymer and (b) one or more of therapeutic or biologically active agents.

56. A composition of claim 55 wherein the polymer is crosslinked and the inhibitor is entrapped within the polymer matrix.

57. A composition of claim 1 additionally containing water.

58. A composition of claim 6 wherein the chemical functionality which has an interactive affinity for target receptors on the transport barrier walls of the digestive tract is a glycoside.

59. A composition of claim 6 wherein the inhibitor is functionalized by reacting said inhibitor with a polymerizable material.

60. A composition of claim 59 wherein the polymerizable material is acryloyl chloride.

61. A composition of claim 6, wherein the chemical functionality that has an interactive affinity for target receptors located on the transport barrier walls of the digestive tract is covalently bonded to said polymer.

62. A composition of claim 6, wherein the chemical functionality that has an interactive affinity for target receptors located on the transport barrier walls of the digestive tract is part of the inhibitor of proteolytic enzymes.

63. A composition of claim 59, wherein the chemical functionality that has an interactive affinity for target receptors located on the transport barrier walls of the digestive tract is covalently bonded to said polymer.

64. A method of claim 39, wherein the chemical functionality that has an interactive affinity for target receptors located on the transport barrier walls of the digestive tract is covalently bonded to said polymer.

65. A method of claim 60 wherein the chemical functionality that has an interactive affinity for target receptors located on the transport barrier walls of the digestive tract is part of the inhibitor of proteolytic enzymes.

66. A composition of claim 1, wherein said chemical functionality is integral to the inhibitor.

67. A composition of claim 1, wherein said chemical functionality is covalently bound to the polymer.

68. A method of claim 39, wherein said chemical functionality is part integral to the inhibitor.

69. A method of claim 39, wherein said chemical functionality is covalently bound to the polymer.

* * * * *